(12) United States Patent
Inagaki et al.

(10) Patent No.: US 10,851,092 B2
(45) Date of Patent: Dec. 1, 2020

(54) PYRIDINE COMPOUND

(71) Applicant: Daiichi Sankyo Company, Limited, Tokyo (JP)

(72) Inventors: Hiroaki Inagaki, Tokyo (JP); Yoshihiro Shibata, Tokyo (JP); Hidenori Namiki, Tokyo (JP); Hideaki Kageji, Tokyo (JP); Kiyoshi Nakayama, Tokyo (JP); Yasuyuki Kaneta, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 62 days.

(21) Appl. No.: 16/337,896

(22) PCT Filed: Sep. 28, 2017

(86) PCT No.: PCT/GB2017/052913
§ 371 (c)(1),
(2) Date: Mar. 28, 2019

(87) PCT Pub. No.: WO2018/060714
PCT Pub. Date: Apr. 5, 2018

(65) Prior Publication Data
US 2020/0039974 A1    Feb. 6, 2020

(30) Foreign Application Priority Data
Sep. 29, 2016   (JP) .................. 2016-191725

(51) Int. Cl.
*C07D 413/14* (2006.01)
*C07D 401/14* (2006.01)
(52) U.S. Cl.
CPC ......... *C07D 413/14* (2013.01); *C07D 401/14* (2013.01)
(58) Field of Classification Search
CPC .................................................. C07D 413/14
USPC ........................................................ 546/153
See application file for complete search history.

(56) References Cited

FOREIGN PATENT DOCUMENTS

| CL | 2018000119 A1 | 6/2018 |
|---|---|---|
| WO | WO 2001/053267 A1 | 7/2001 |
| WO | WO 2005/023761 A2 | 3/2005 |
| WO | WO 2007/099317 A1 | 9/2007 |
| WO | WO 2007/099323 A2 | 9/2007 |
| WO | WO 2007/113548 A1 | 10/2007 |
| WO | WO 2007/113565 A1 | 10/2007 |
| WO | WO 2011/022473 A1 | 2/2011 |
| WO | WO 2011/133728 A2 | 10/2011 |
| WO | WO 2012/082817 A1 | 6/2012 |
| WO | WO 2014/012050 A2 | 1/2014 |
| WO | WO 2014/141187 A1 | 9/2014 |
| WO | WO 2015/031613 A1 | 3/2015 |
| WO | WO 2015/079251 A1 | 6/2015 |
| WO | WO 2016/061280 A1 | 4/2016 |
| WO | WO 2017/011776 A1 | 1/2017 |

OTHER PUBLICATIONS

International Search Report and Written Opinion, dated Nov. 14, 2017, in connection with Application No. PCT/GB2017/052913.
International Preliminary Report on Patentability, dated Apr. 2, 2019, in connection with Application No. PCT/GB2017/052913.
Agrawal et al., Exomic Sequencing of Medullary Thyroid Cancer Reveals Dominant and Mutually Exclusive Oncogenic Mutations in RET and RAS. The Journal of Clinical Endocrinology and Metabolism. Feb. 1, 2013; 98(2):E364-9.
Ashman et al., Therapeutic targeting of c-KIT in cancer. Expert Opinion on Investigational Drugs. Jan. 1, 2013; 22(1): 103-15.
Carlomagno et al., Point Mutation of the RetProto-oncogene in the TT Human Medullary Thyroid Carcinoma Cell Line. Biochemical and Biophysical Research Communications. Feb. 27, 1995; 207(3): 1022-8.
George, Targeting PDGF Receptors in Cancer—Rationales and Proof of Concept Clinical Trials. New Trends in Cancer for the 21$^{st}$ Century. In: Advances in Experimental Medicine and Biology. 2003; 532: 141-51.
Hayman et al., VEGF Inhibition, Hypertension, and Renal Toxicity. Current Oncology Reports. Aug. 2012; 14(4):285-94.
Heinrich, Targeting FLT3 Kinase in Acute Myelogenous Leukemia: Progress, Perils, and Prospects. Mini-Reviews in Medicinal Chemistry. Mar. 1, 2004; 4(3):255-71.
Kodama et al., Alectinib Shows Potent Antitumor Activity against RET-Rearranged Non-Small Cell Lung Cancer. Molecular Cancer Therapeutics. Dec. 2014; 13 (12):2910-8.
Kohno et al., KIF5B-RET fusions in lung adenocarcinoma. Nature Medicine. Mar. 2012; 18(3), 375-7.
Le Rolle et al., Identification and characterization of RET fusions in advanced colorectal cancer. Oncotarget. Oct. 6, 2015; 6(30):28929-37.

(Continued)

*Primary Examiner* — Nizal S Chandrakumar
(74) *Attorney, Agent, or Firm* — Wolf, Greenfield & Sacks, P.C.

(57) ABSTRACT

The present invention relates to a compound having RET kinase inhibiting action or a pharmaceutically acceptable salt thereof, useful in the treatment of diseases such as cancer. In particular a compound represented by the following general formula (I) as defined herein: (I) or a pharmaceutically acceptable salt thereof.

(I)

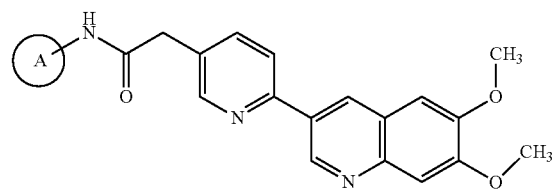

13 Claims, 2 Drawing Sheets

(56) References Cited

OTHER PUBLICATIONS

Levitzki, PDGF receptor kinase inhibitors for the treatment of PDGF driven diseases. Cytokine & Growth Factor Reviews. Aug. 1, 2004; 15(4):229-35.

Matsubara et al., Identification of CCDC6-RET fusion in the human lung adenocarcinoma cell line, LC-2/ad. Journal of Thoracic Oncology. Dec. 1, 2012; 7(12):1872-6.

Medico et al., The molecular landscape of colorectal cancer cell lines unveils clinically actionable kinase targets. Nature Communications. Apr. 30, 2015; 6(Article No. 7002): 10 pages.

Mulligan, RET revisited: expanding the oncogenic portfolio. Nature Reviews Cancer. Mar. 2014; 14(3): 173-86.

Phay et al., Targeting RET Receptor Tyrosine Kinase Activation in Cancer. Clinical Cancer Research. Dec. 2010; 16(24):5936-41.

Rowbottom et al., Identification of 1-(3-(6, 7-dimethoxyquinazolin-4-yloxy) phenyl)-3-(5-(1, 1, 1-trifluoro-2-methylpropan-2-yl) isoxazol-3-yl) urea hydrochloride (CEP-32496), a highly potent and orally efficacious inhibitor of V-RAF murine sarcoma viral oncogene homologue B1 (BRAF) V600E. J Medicinal Chemistry. Jan. 23, 2012;55(3):1082-1105.

Sherman, Lessons learned and questions unanswered from use of multitargeted kinase inhibitors in medullary thyroid cancer. Oral Oncology. Jul. 1, 2013;49(7):707-10.

Wang et al., Trk kinase inhibitors as new treatments for cancer and pain. Expert Opinion on Therapeutic Patents. Mar. 1, 2009; 19(3):305-19.

PYRIDINE COMPOUND

RELATED APPLICATIONS

This application is a national stage filing under 35 U.S.C. § 371 of international PCT application, PCT/GB2017/052913, filed Sep. 28, 2017, which claims priority under 35 U.S.C. § 119(a) to Japanese Application, 2016-191725, filed Sep. 29, 2016, each of which is incorporated herein by reference.

TECHNICAL FIELD

The present invention relates to a compound which has selective inhibitory activity on RET kinase, PDGFR kinase, KIT kinase, NTRK kinase, FLT3 kinase and the like and is useful for the treatment of cancer, or a salt thereof.

The present invention relates to a preventive agent and/or a therapeutic agent for lung cancer, thyroid gland cancer, breast cancer, colon cancer, sarcoma, leukemia, etc., which comprise, as an active ingredient, the aforementioned compound or a salt thereof.

Moreover, the present invention relates to a composition for preventing or treating the aforementioned diseases, which comprises, as an active ingredient, the aforementioned compound or a salt thereof, use of the aforementioned compound for the production of a medicament for preventing or treating the aforementioned diseases, or a method for preventing or treating the aforementioned diseases, which comprises administering a pharmacologically effective amount of the aforementioned compound to a mammal (preferably, a human).

BACKGROUND ART

RET kinase, PDGFR (platelet-derived growth factor receptor) kinase, KIT (stem cell factor receptor) kinase, NTRK (neurotrophic factor receptor) kinase, FLT3 kinase, and the like are all receptor tyrosine kinases. These kinases have a structure of penetrating the cell membrane, and have a growth factor-binding site outside the cell and a tyrosine kinase active site inside the cell. These receptor tyrosine kinases convert stimulation by a growth factor from outside of the cell (=binding to a growth factor-binding site) to signals into the cells (=phosphorylation of downstream protein), and play a role for the growth, division, differentiation and morphogenesis of cells). The activating mutation (including point mutation, deletion mutation, insertion mutation, fusion mutation, etc.) or increased expression of these kinases is considered to cause a large number of cancer, sarcoma, leukemia, and the like, and thus, inhibitors for these kinases are considered to be effective for the treatment of cancer, sarcoma, leukemia, and the like (Non Patent Literatures 1 to 5 and Patent Literature 1).

In particular, with respect to RET kinase, its activating mutation has been found in some lung cancer patients, thyroid gland cancer patients and the like (Non Patent Literatures 6 to 8), and these patients do not have other mutations. Hence, the mutated RET kinase is considered to be a driver mutation for these cancers. That is to say, it is considered that, if a patient with RET kinase mutation is precisely detected and a RET kinase inhibitor having sufficient inhibitory activity is then administered to the patient, the cancer can be treated with high probability. Recently, it has been suggested that the activating mutation of RET kinase cause cancer growth not only in lung cancer and thyroid gland cancer, but also in several types of breast cancer and colon cancer (Non Patent Literatures 9 to 11).

To date, agents having RET kinase inhibiting activity, such as cabozantinib, vandetanib and lenvatinib, have been used for RET-mutated cancer patients, but the therapeutic effects of such agents have been weak and restrictive (Non Patent Literature 12). It has been considered that such low therapeutic effects of these agents are attributable to low RET kinase inhibiting activity of these compounds, and toxicity (Non Patent Literature 13) such as hypertension based on inhibition of KDR kinase (alias: VEGFR2 kinase) (Non Patent Literature 14).

Moreover, the previously reported RET kinase inhibitory compounds including the aforementioned existing agents have weak inhibitory activity on gatekeeper mutated kinase, which is a representative mutated kinase being resistant to kinase inhibitors (Non Patent Literature 15), and thus, even though such a compound is used in treatment, cancer gains resistance to the compound in an early stage, so that the cancer becomes untreatable.

Several RET inhibitors have been reported so far (Patent Literatures 1 and 2). However, these RET inhibitors are problematic in terms of low RET kinase inhibiting activity, high KDR kinase inhibiting activity, inapplicability to RET gatekeeper mutants, and the like.

CITATION LIST

Patent Literature

[Patent Literature 1] International Publication No. WO 2015/031613
[Patent Literature 2] International Publication No. WO 2015/079251

Non Patent Literature

[Non Patent Literature 1] Levitzki, A. Cytokine & Growth Factor Reviews, 2004, 15 (4), pp. 229-235.
[Non Patent Literature 2] George, D. Advances in Experimental Medicine and Biology, 2003, 532, pp. 141-151.
[Non Patent Literature 3] Ashman, L. K. and Griffith, R. Expert Opinion on Investigational Drugs, 2013, 22 (1), pp. 103-115.
[Non Patent Literature 4] Wang, T. et al. Expert Opinion on Therapeutic Patents, 2009, 19 (3), pp 305-319.
[Non Patent Literature 5] Heinrich, M. C. Mini-Reviews in Medicinal Chemistry, 2004, 4 (3), pp. 255-271.
[Non Patent Literature 6] Kohno, T. et al. Nature Medicine, 2012, 18 (3), pp. 375-377.
[Non Patent Literature 7] Matsubara, D. et al. Journal of Thoracic Oncology, 2012, 7 (12), pp. 1872-1876.
[Non Patent Literature 8] Agrawal, N. et al. The Journal of clinical endocrinology and metabolism, 2013, 98 (2), E364-E369.
[Non Patent Literature 9] Mulligan, L. M. Nature Reviews Cancer, 2014, 14 (3), pp. 173-186.
[Non Patent Literature 10] Le Rolle, A. F. et al. Oncotarget, 2015, 6 (30), pp. 28929-28937.
[Non Patent Literature 11] Medico, E. et al. Nature Communications, 2015, 6, Article No. 7002.
[Non Patent Literature 12] Phay, J. E. and Shah, M. H. Clinical Cancer Research, 2010, 16(24), pp. 5936-5941.
[Non Patent Literature 13] Hayman, S. R. et al. Current Oncology Reports, 2012, 14 (4), pp. 285-294.
[Non Patent Literature 14] Sherman, S. I. Oral Oncology, 2013, 49, pp. 707-710.

[Non Patent Literature 15] Kodama, T. et al. Molecular Cancer Therapeutics, 2014, 13, pp. 2910-2918.

SUMMARY OF INVENTION

The present invention provides a therapeutic agent, for example, an anticancer agent, for various types of cancer, sarcoma, leukemia and the like caused by the activating mutation or increased expression of kinase, wherein these diseases are caused by RET kinase and the existing inhibitors exhibit insufficient therapeutic effects on these diseases.

The present inventors have thought that, if an agent that is much stronger and has higher kinase selectivity than existing drugs were developed and/or applied to diseases caused by the activating mutation or increased expression of kinase, such as RET kinase, on which the existing inhibitors exhibit insufficient therapeutic effects, among kinases whose activating mutation or increased expression causes various types of cancer, sarcoma, leukemia, etc., the agent could provide high therapeutic effects on the diseases, and thus, they have conducted intensive studies to find such an agent.

Consequently, the present inventors have found that the after-mentioned compound represented by formula (I) exhibits strong and selective inhibitory activity on kinases such as RET, PDGFR, KIT, NTRK, and FLT3, and also exhibits strong inhibitory activity on their gatekeeper mutants. Moreover, the inventors have also found that since this compound has weak inhibitory activity on KDR kinase that seems to express toxicity when it is inhibited, and has excellent kinase selectivity, this compound is useful as a pharmaceutical product.

That is to say, the present inventors have found that the compound represented by formula (I) can be used as a medicament that is a safe and useful preventive/therapeutic agent for cancers, or such cancer-related pathologic conditions or diseases, which have the activating mutation of kinases such as RET, PDGFR, KIT, NTRK and FLT3, or are attended with the increased expression of these kinases. Based on these findings, the inventors have completed the present invention.

The compound of the present invention has extremely strong and selective inhibitory activity, particularly, on RET kinase, and is useful as a therapeutic agent for cancers (in particular, lung cancer, thyroid gland cancer, etc.).

Furthermore, since the compound of the present invention has an aromatic ring nitrogen atom(s) exhibiting weak basicity in its structure, it has high water solubility particularly in an acidic region, when compared with neutral compounds such as the compounds disclosed in International Publication No. WO 2015/031613. Further, since highly water-soluble salts can be formed by utilizing the aromatic ring nitrogen atoms of the aforementioned compound, the compound can be expected to have high oral absorbability and is extremely useful as a pharmaceutical product.

The present invention relates to the following (1) to (17):
(1) A compound represented by the following general formula (I):

[Formula 1]

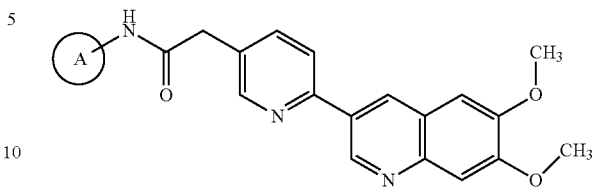

(I)

wherein A represents one selected from the following formulae (Ia) to (Id):

[Formula 2]

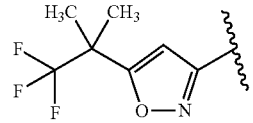

(Ia)

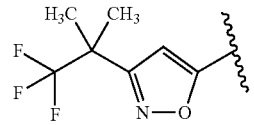

(Ib)

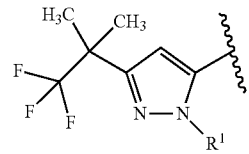

(Ic)

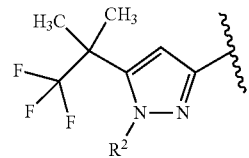

(Id)

wherein $R^1$ represents a hydrogen atom or a C1-C3 alkyl group, and $R^2$ represents a hydrogen atom or a C1-C3 alkyl group, or a pharmaceutically acceptable salt thereof.
(2) One or two or more compounds selected from the compounds represented by the following structural formulae:

[Formula 3]

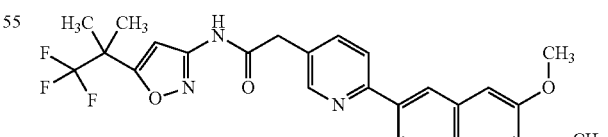

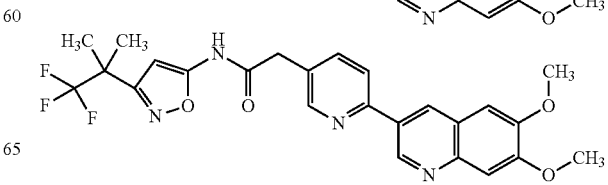

-continued

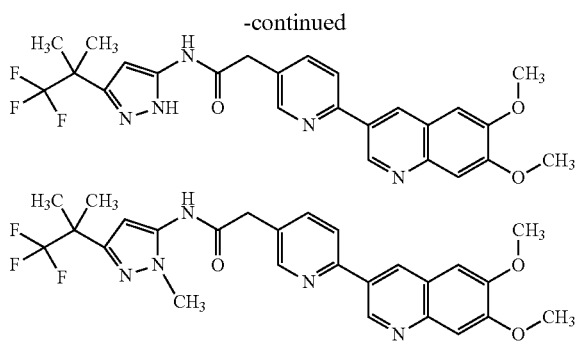

(3) 2-[6-(6,7-Dimethoxyquinolin-3-yl)pyridin-3-yl]-N-[5-(1,1,1-trifluoro-2-methylpropan-2-yl)-1,2-oxazol-3-yl]acetamide,
(3-1) a compound having the following structural formula or a pharmaceutically acceptable salt thereof.

[Formula 4]

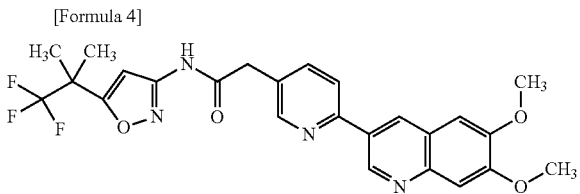 [SMILES: COc1cc2cc(-c3ccc(CC(=O)Nc4cc(C(C)(C)C(F)(F)F)on4)cn3)cnc2cc1OC]

(4) 2-[6-(6,7-Dimethoxyquinolin-3-yl)pyridin-3-yl]-N-[3-(1,1,1-trifluoro-2-methylpropan-2-yl)-1,2-oxazol-5-yl]acetamide,
(4-1) a compound having the following structural formula or a pharmaceutically acceptable salt thereof.

[Formula 5]

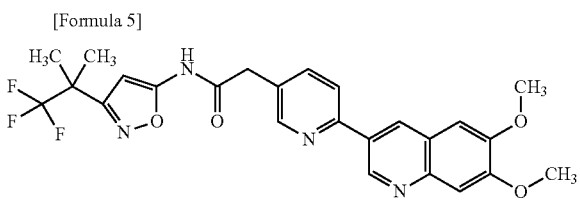

(5) 2-[6-(6,7-Dimethoxyquinolin-3-yl)pyridin-3-yl]-N-[3-(1,1,1-trifluoro-2-methylpropan-2-yl)-1H-pyrazol-5-yl]acetamide,
(5-1) a compound having the following structural formula or a pharmaceutically acceptable salt thereof.

[Formula 6]

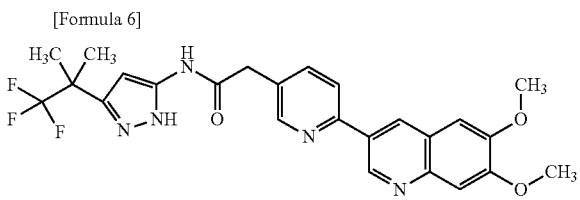 [SMILES: COc1cc2cc(-c3ccc(CC(=O)Nc4cc(C(C)(C)C(F)(F)F)n[nH]4)cn3)cnc2cc1OC]

(6) 2-[6-(6,7-Dimethoxyquinolin-3-yl)pyridin-3-yl]-N-[1-methyl-3-(1,1,1-trifluoro-2-methylpropan-2-yl)-1H-pyrazol-5-yl]acetamide,
(6-1) a compound having the following structural formula or a pharmaceutically acceptable salt thereof.

[Formula 7]

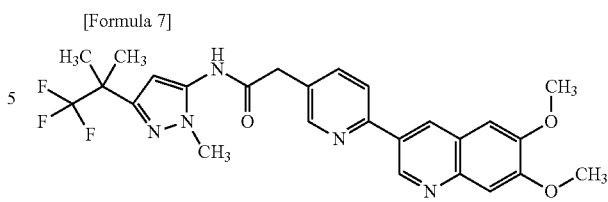

(7) A pharmaceutically acceptable salt of the compound according to any one of the above (2) to (6).
(8) A methanesulfonate salt of the compound according to any one of the above (2) to (6).
(9) A RET kinase inhibitor comprising, as an active ingredient, the compound according to any one of the above (1) to (8) or a pharmaceutically acceptable salt thereof.
(10) A medicament comprising, as an active ingredient, the compound according to any one of the above (1) to (8) or a pharmaceutically acceptable salt thereof.
(11) The medicament according to claim 10 for treating a disease caused by activating mutation or increased expression of RET kinase, a disease associated with the activating mutation of RET kinase, or a disease attended with the activating mutation of RET kinase.
(12) The medicament according to the above (10) for use in the prevention or treatment of cancer.
(12-1) The medicament according to the above (10) for use in the treatment of cancer.
(13) The medicament according to the above (10) for use in the treatment of cancer caused by the activating mutation or increased expression of RET kinase.
(14) The medicament according to the above (10) for use in the treatment of lung cancer, thyroid gland cancer, breast cancer or colon cancer.
(15) Use of the compound according to any one of the above (1) to (8) or a pharmaceutically acceptable salt thereof for the production of a pharmaceutical composition.
(16) A method for treating or preventing cancer, comprising administering a pharmacologically effective amount of the compound according to any one of the above (1) to (8) or a pharmaceutically acceptable salt thereof to a warm-blooded animal.
(17) The compound according to any one of the above (1) to (8) or a pharmaceutically acceptable salt thereof, for use in a method for treating or preventing disease.

In the present invention, the "C1-C3 alkyl group" means a linear or branched alkyl group having 1 to 3 carbon atoms, and examples of the C1-C3 alkyl group can include a methyl, ethyl, n-propyl or isopropyl group. In $R^1$ and $R^2$, the C1-C3 alkyl group is preferably a methyl group. In $P^2$, the C1-C3 alkyl group is preferably a methyl group or an ethyl group.

In the present invention, the "halogen atom" means a fluorine atom, a chlorine atom, a bromine atom, or an iodine atom. In $X^1$, $X^2$, $X^3$ and $X^4$, the halogen atom is preferably a chlorine atom or a bromine atom.

In the present invention, the "monovalent metal" is preferably lithium, sodium, or potassium.

In the present invention, when the present compound has a basic group such as an amino group, it can be converted to a salt by being reacted with an acid, or when the present compound has an acidic group such as a carboxyl group, it can be converted to a salt by being reacted with a base. Accordingly, the "pharmaceutically acceptable salt" means the thus formed salt.

Preferred examples of the salts based on a basic group can include: hydrohalides such as hydrofluoride, hydrochloride, hydrobromide and hydroiodide, inorganic acid salts such as nitrate, perchlorate, sulfate and phosphate; lower alkanesulfonates such as methanesulfonate, trifluoromethanesulfonate and ethanesulfonate, arylsulfonates such as benzenesulfonate and p-toluenesulfonate, organic acid salts such as acetate, malate, fumarate, succinate, adipate, citrate, ascorbate, tartrate, oxalate and maleate; and amino acid salts such as glycine salt, lysine salt, arginine salt, ornithine salt, glutamate and aspartate. The salts based on a basic group are preferably hydrohalides or inorganic acid salts.

On the other hand, preferred examples of the salts based on an acidic group can include: alkali metal salts such as sodium salt, potassium salt and lithium salt, alkaline earth metal salts such as calcium salt and magnesium salt, metal salts such as aluminum salt and iron salt; amine salts including inorganic salts such as ammonium salt, and organic salts such as tert-butylamine salt, t-octylamine salt, diisopropylamine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt and tris (hydroxymethyl)aminomethane salt; and amino acid salts such as glycine salt, lysine salt, arginine salt, ornithine salt, glutamate and aspartate. More preferred examples can include magnesium salt, calcium salt, diisopropylamine salt and tert-butylamine salt, and a particularly preferred example can be tert-butylamine salt.

The compound represented by general formula (I) of the present invention or a pharmaceutically acceptable salt thereof includes all of isomers (keto-enol isomers, stereoisomers, etc.).

When the compound represented by general formula (I) of the present invention or a pharmaceutically acceptable salt thereof has an asymmetric carbon atom in the molecule thereof, it has various isomers. In the case of the compound of the present invention, these isomers and mixture of these isomers are all represented by a single formula, namely, general formula (I). Therefore, the present invention includes all of these isomers, and mixtures comprising these isomers at any given ratio.

The above described stereoisomer can be obtained by isolating the synthesized compound according to the present invention, as desired, according to an ordinary optical resolution method or separation method.

The compound represented by general formula (I) of the present invention or a pharmaceutically acceptable salt thereof may contain a non-natural ratio of atomic isotopes in one or more atoms constituting such a compound. Examples of such atomic isotopes can include deuterium ($^2H$), tritium ($^3H$), iodine-125 ($^{125}I$), carbon-13 ($^{13}C$) and carbon-14 ($^{14}C$). In addition, the above described compound can be radiolabeled with a radioisotope such as tritium ($^3H$), iodine-125 ($^{125}I$) or carbon-14 ($^{14}C$). The radiolabeled compound is useful as a therapeutic or preventive agent, a research reagent such as an assay reagent, and a diagnostic agent such as an in vivo diagnostic imaging agent. The isotope mutants of the compound of the present invention are all included in the scope of the present invention, regardless of whether or not they are radioactive.

When the compound represented by general formula (I) of the present invention or a pharmaceutically acceptable salt thereof is left in the air or is recrystallized, it absorbs water, or adsorbed water is attached thereto, or it becomes a hydrate in some cases. Such a hydrate is also included in the salt of the present invention.

The compound represented by general formula (I) of the present invention or a pharmaceutically acceptable salt thereof sometimes absorbs another certain type of solvent and thereby becomes a solvate. Such a solvate is also included in the salt of the present invention.

Furthermore, the present invention includes all of compounds which are metabolized in vivo and are converted to the above described pyridine compounds represented by general formula (I) or the salts thereof.

Next, representative methods for producing the compound represented by general formula (I) will be described below. The compound of the present invention can be produced by various production methods, and the following production methods are given only as examples of the present production method, and the present invention should not be limited to these production methods. It is to be noted that, upon the reaction, substituents can be protected by suitable protecting groups, as necessary, and that the type of such a protecting group is not particularly limited. Commercially available starting materials and reagents have been used without further purification, unless otherwise specified.

Method A: The above described compound represented by general formula (I) can be synthesized by condensation reaction of an amine compound (1) with a carboxylic acid compound (2), as shown in the following formula 1.

<Formula 1>
[Formula 8]

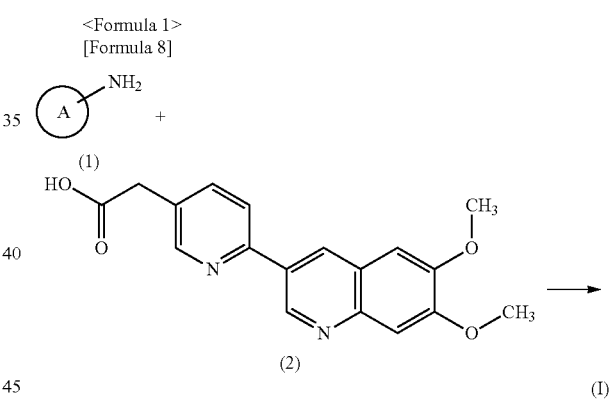

wherein A is defined above.
(A-1) Amine Compound (1)

As an amine compound (1) used in the present reaction, the following compounds (1a) to (1d) can be used. The compounds (1a) and (1b) can be synthesized in accordance with the method described in J. Med. Chem., 2012, 55, 1082-1105. The amine compounds (1c) and (1d) can be synthesized in accordance with the method described in the second step of Example 42, Section 155 of WO 2014/141187.

[Formula 9]

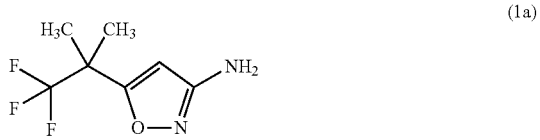

-continued

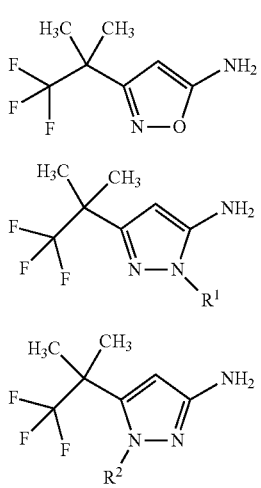

wherein $R^1$ and $R^2$ are defined above.
(A-2) Carboxylic Acid Compound (2)
(A-2-1) Production Method 1 of Carboxylic Acid Compound (2)

<Formula 2>
[Formula 10]

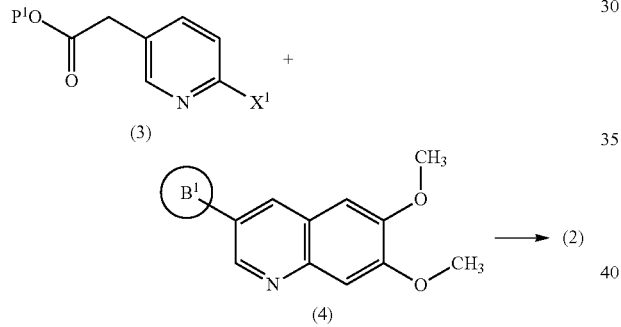

wherein $P^1$ represents a hydrogen atom or a carboxylic acid protecting group, $B^1$ represents boronic acid, a boronic acid ester, boronic acid pinacolate, a trifluoroborate potassium salt, cyclic triolborate, or MIDA boronate, and $X^1$ represents a halogen atom.

The carboxylic acid compound (2) can be synthesized, for example, by performing a Suzuki coupling reaction using a 2-halopyridine acetic acid derivative (3) and a quinoline-3-boronic acid derivative (4), as shown in the above formula (2). When $P^1$ is a carboxylic acid protecting group, after completion of the Suzuki coupling reaction, the resultant is subjected to a deprotection reaction such as a hydrolysis reaction so that the reaction product can be led to the carboxylic acid compound (2).

Regarding the carboxylic acid protecting group, suitable protecting groups can be determined with reference to Peter G. M. Wuts, Theodora W. Greene, Greene's Protecting Groups in Organic Synthesis, 4th edition, Wiley-Interscience, 2006, and the like. The protecting group $P^1$ is preferably a methyl group, an ethyl group or a t-butyl group. Regarding the deprotection reaction, suitable reaction conditions can be determined depending on the type of a protecting group used, with reference to Peter G. M. Wuts, Theodora W. Greene, Greene's Protecting Groups in Organic Synthesis, 4th edition, Wiley-Interscience, 2006, and the like.

(A-2-1-1) Production Method of 2-Halopyridine Acetic Acid Derivative (3)

With regard to the 2-halopyridine derivative (3) as a staring material used in the present reaction, a commercially available compound can be used, or it can be synthesized according to a known method. Alternatively, instead of the 2-halopyridine derivative (3), a 2-(trifluoromethanesulfonyloxy)pyridine derivative, or 2-(substituted sulfonyloxy)pyridine derivatives such as a 2-(p-toluenesulfonyloxy)pyridine derivative and a 2-(methanesulfonyloxy)pyridine derivative, can be used.

Preferred examples of the 2-halopyridine derivative (3) include 2-chloropyridin-5-ylacetic acid, methyl 2-chloropyridin-5-yl acetate, ethyl 2-chloropyridin-5-yl acetate, and t-butyl 2-chloropyridin-5-yl acetate.

(A-2-1-2) Production Method of Quinoline-3-Boronic Acid Derivative (4)

Examples of the quinoline-3-boronic acid derivative (4) can include compounds (4a) to (40, as shown in the following formula 3, but the examples are not limited to.

<Formula 3>
[Formula 11]

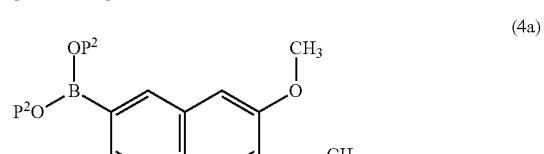

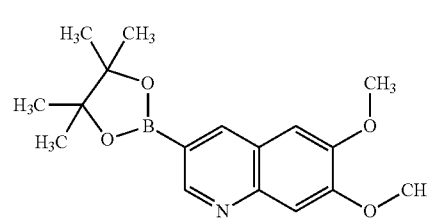

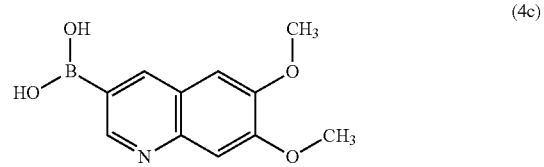

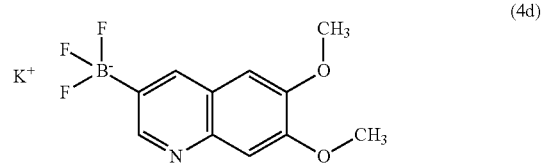

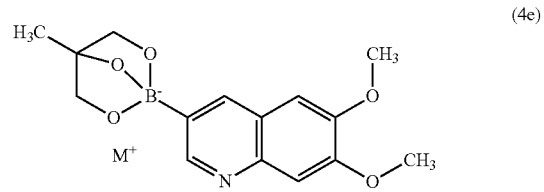

-continued

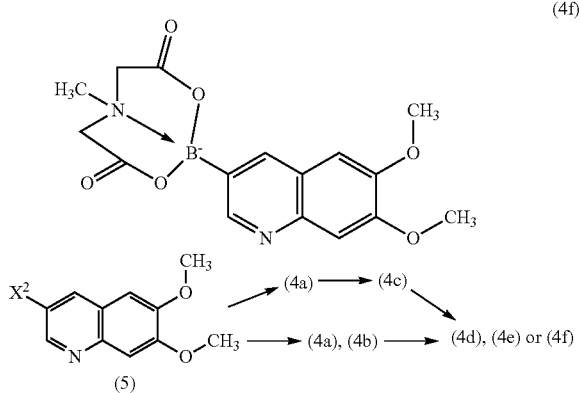

wherein $P^2$ represents a C1-C3 alkyl group, $X^2$ represents a halogen atom, and M represents a monovalent metal.

The quinoline-3-boronic acid derivatives (4a), (4b) and (4c) can be synthesized from the 3-haloquinoline (5) shown in the above formula 3. For example, n-butyllithium is allowed to act on the 3-haloquinoline (5) that can be synthesized according to a known method, to obtain a 3-lithioquinoline derivative, and thereafter, trialkyl borate such as triisopropyl borate is allowed to act on the 3-lithioquinoline derivative to synthesize the quinoline-3-boronic acid ester derivative (4a). Moreover, the quinoline-3-boronic acid ester derivative (4a) is hydrolyzed, so that it can be led to the quinoline-3-boronic acid derivative (4c). Otherwise, bis(pinacolato)diboron is allowed to act on the 3-haloquinoline (5) in the presence of a palladium catalyst, so that the 3-haloquinoline (5) can be led to the quinoline-3-boronic acid ester derivative (4b).

Furthermore, instead of the quinoline-3-boronic acid derivative (4c) or the quinoline-3-boronic acid ester derivatives (4a) and (4b), the trifluoroborate potassium salt (4d), the cyclic triolborate (4e), or the MIDA boronate (4f) can also be used. The trifluoroborate potassium salt (4d), the cyclic triolborate(4e), and the MIDA boronate (4f) can be synthesized by using the quinoline-3-boronic acid derivative (4c) or the quinoline-3-boronic acid ester derivatives (4a) and (4b) as raw materials according to a known method.

After completion of the synthesis, the quinoline-3-boronic acid derivatives (4a) to (4f) may be isolated, or may be directly subjected to a Suzuki coupling reaction, without performing isolation and purification.

(A-2-1-3) Suzuki Coupling Reaction of 2-Halopyridine Acetic Acid Derivative (3) with Quinoline-3-Boronic Acid Derivative (4)

In the present reaction, a catalyst containing palladium can be used. Examples of the catalyst that can be used herein can include tetrakis(triphenylphosphine)palladium(0), bis[tris(2-methylphenyl)phosphine]palladium(0), bis(tri-tert-butylphosphine)palladium(0), bis(tricyclohexylphosphine)palladium(0), bis(triphenylphosphine)palladium(II) dichloride, [1,1'-bis(diphenylphosphino)ferrocene]dichloropalladium(II), dichlorobis(tri-o-tolylphosphine)palladium(II), dichlorobis(tricyclohexylphosphine)palladium(II), dichloro[2,2'-bis(diphenylphosphino)-1,1'-binaphthyl]palladium(II), dichloro[9,9-dimethyl-4,5-bis(diphenylphosphino)xanthene]palladium(II), [1,3-bis(2,6-diisopropylphenyl)imidazol-2-ylidene](3-chloropyridyl)palladium(II) dichloride (PEPSI (registered trademark)-IPr catalyst), chloro(2-dicyclohexylphosphino-2',6'-dimethoxy-1,1'-biphenyl)[2-(2-aminoethyl)phenyl]palladium(II) (SPhos Pd G1), chloro(2-dicyclohexylphosphino-2',4',6'-triisopropyl-1,1'-biphenyl)[2-(2-aminoethyl)phenyl]palladium(II) (XPhos Pd G1), chloro(triphenylphosphine)[2-(2'-amino-1,1'-biphenyl)]palladium(II), chloro[tri(o-tolyl)phosphine][2-(2'-amino-1,1'-biphenyl)]palladium(II), chloro[(tricyclohexylphosphine)-2-(2'-amino1,1'-biphenyl)]palladium(II) (PCy3 Pd G2), chloro[(tri t-butylphosphine)-2-(2'-amino-1,1'-biphenyl)]palladium(II) (P(tBu)$_3$ Pd G2), chloro(2-dicyclohexylphosphino-2',6'-dimethoxy-1,1'-biphenyl)[2-(2'-amino-1,1'-biphenyl)]palladium(II) (SPhos Pd G2), chloro(2-dicyclohexylphosphino-2',4',6'-triisopropyl-1,1'-biphenyl)[2-(2'-amino-1,1'-biphenyl)]palladium(II) (XPhos Pd G2), [2,2'-bis(diphenylphosphino)-1,1'-binaphthyl][2-(2'-amino-1,1'-biphenyl)]palladium(II) methanesulfonate (rac-BINAP Pd G3), (2-dicyclohexylphosphino-2',6'-dimethoxybiphenyl)[2-(2'-amino-1,1'-biphenyl)]palladium(II) methanesulfonate (SPhos Pd G3), [(4,5-bis(diphenylphosphino)-9,9-dimethylxanthene)-2-(2'-amino-1,1'-biphenyl)]palladium(II) methanesulfonate (XantPhos Pd G3), (2-dicyclohexylphosphino-2',4',6'-triisopropyl-1,1'-biphenyl)[2-(2'-amino-1,1'-biphenyl)]palladium(II) methanesulfonate (XPhos Pd G3), palladium(II) acetate, Tris(dibenzylideneacetone)dipalladium(0), and a palladium carbon catalyst.

Together with the above described palladium catalyst, a ligand can be selected and used, as necessary. Examples of the ligand can include triphenylphosphine, tri(o-tolyl)phosphine, tri(t-butyl)phosphine, tri(cyclohexyl)phosphine, 1,1'-bis(diphenylphosphino)ferrocene (DPPF), 1,2-bis(diphenylphosphino)ethane (DPPE), 2,2'-bis(diphenylphosphino)-1,1'-binaphthalene (rac-BINAP), 4,5-bis(diphenylphosphino)-9,9-dimethylxanthene (XantPhos), 2-dicyclohexylphosphino-2',6'-dimethoxybiphenyl (SPhos), and 2-dicyclohexylphosphino-2',4',6'-triisopropylbiphenyl (XPhos).

A base may be used in the present reaction, as necessary. Examples of the base that can be used herein can include sodium hydrogen carbonate, potassium hydrogen carbonate, sodium carbonate, potassium carbonate, cesium carbonate, sodium hydroxide, potassium hydroxide, thallium hydroxide, potassium phosphate, cesium fluoride, potassium t-butoxide, triethylamine, and diisopropylethylamine, but the examples are not limited thereto.

For the purpose of accelerating the reaction or suppressing generation of by-products, additives can be added to the reaction system, as appropriate. For example, when a triflate body is used as a raw material, lithium chloride can be added, and also, for suppression of generation of by-products, potassium formate or the like can be added.

An aqueous solvent system is preferably used in the present reaction. However, the present reaction can also be carried out without using water. Examples of the solvent can include alcohols such as methanol, ethanol, 1-propanol, 2-propanol and 1-butanol, ethers such as tetrahydrofuran, 2-methyltetrahydrofuran and 1,4-dioxane, other solvents such as N,N-dimethylformamide, N,N-dimethylacetamide, N-methylpyrrolidone, dimethyl sulfoxide, toluene, benzene, acetonitrile, dichloromethane, 1,2-dichloroethane, chloroform and ethyl acetate, and a mixed solvent of the aforementioned solvent and water. The types of solvents used are not limited to the aforementioned solvents.

Regarding the reaction temperature, the reaction can be carried out at a suitable temperature, depending on the reaction substrate and reagent used. The reaction can be carried out at a temperature from room temperature to 180° C., and more preferably at a temperature from 60° C. to 140° C.

Regarding the reaction time, the reaction can be carried out for a suitable period of time, depending on the reaction substrate and reagent used. The reaction time is preferably from 30 minutes to 6 hours.

(A-2-2) Production Method 2 of Carboxylic Acid Compound (2).

The carboxylic acid compound (2) can also be synthesized by the Suzuki coupling reaction of a pyridine-2-boronic acid derivative (6) with a 3-haloquinoline (5), as shown in the following formula 4.

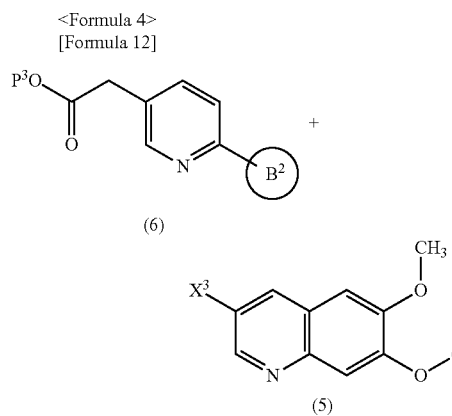

<Formula 4>
[Formula 12]

wherein $B^2$ represents boronic acid, a boronic acid ester, boronic acid pinacolate, a trifluoroborate potassium salt, cyclic triolborate, or MIDA boronate, $P^3$ represents a hydrogen atom or a carboxylic acid protecting group, and $X^3$ represents a halogen atom.

In the present reaction, a boronic acid portion of the pyridine-2-boronic acid derivative (6) may be boronic acid, a boronic acid ester, boronic acid pinacolate, a trifluoroborate potassium salt, cyclic triolborate, or MIDA boronate, as with the quinoline-3-boronic acid derivative (4) in the above described (A-2-1), and further, the same reaction conditions as those used in the above described (A-2-1) can be applied.

Such a boronic acid derivative can be synthesized, for example, from a commercially available 2-halopyridine derivative (3) according to the method regarding the quinoline-3-boronic acid derivative (4) that is described in the above (A-2-1).

Regarding the carboxylic acid protecting group $P^3$, protection and deprotection can be carried out in accordance with the above described (A-2-1).

The coupling reaction of the pyridine-2-boronic acid derivative (6) with the 3-haloquinoline (5) is not limited to the above described Suzuki coupling reaction, and other various cross-coupling reactions can also be used. For example, a cross-coupling reaction of using an organic zinc compound instead of a boronic acid derivative (Negishi reaction) or a cross-coupling reaction of using organic tin (Stille reaction) can be used.

Deprotection reaction of the carboxylic acid protecting group can be carried out in accordance with the method of the above described (A-2-1).

(A-2-3) Production Method 3 of Carboxylic Acid Compound (2)

The carboxylic acid compound (2) can also be synthesized by the method shown in the following formula 5. Specifically, the carboxylic acid compound (2) can be synthesized by constructing a quinoline ring according to a reaction between an amino aldehyde derivative (8) and an acetylene derivative (9).

<Formula 5>
[Formula 13]

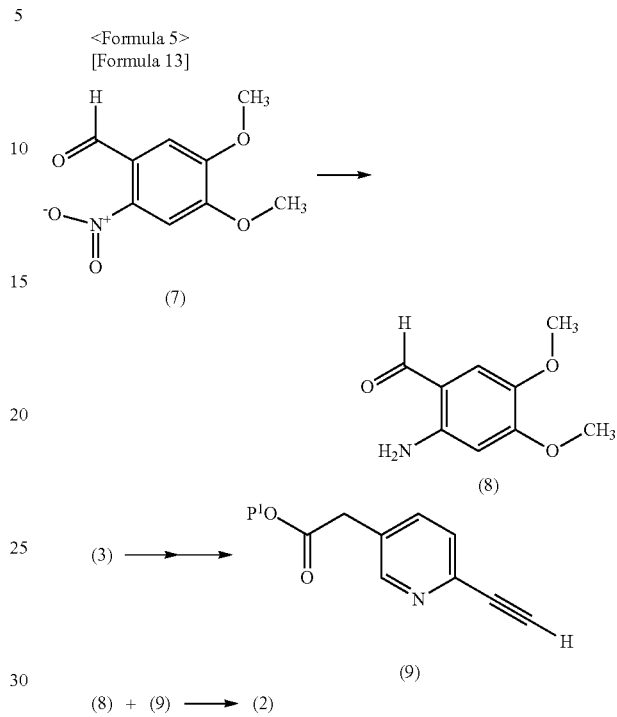

wherein $P^1$ is defined above.

Regarding the carboxylic acid protecting group $P^1$, protection and deprotection can be carried out in accordance with the method of the above described (A-2-1).

(A-2-3-1) Synthesis of Amino Aldehyde Derivative (8)

The amino aldehyde derivative (8) can be synthesized, for example, from the nitro aldehyde derivative (7) or the like, according to a known method. From the nitro aldehyde derivative (7), the amino aldehyde derivative (8) can be synthesized by a publicly known method used in the reduction of a nitro group. Examples of the reduction method can include catalytic hydrogenation reduction, a method of using iron powders in the presence of an acid such as hydrochloric acid or acetic acid, and a method of using tin(II) chloride.

(A-2-3-2) Synthesis of Acetylene Derivative (9)

The acetylene derivative (9) can be synthesized by performing a Sonogashira coupling reaction between the 2-halopyridine derivative (3) or the like and mono-silyl protected acetylene, and then removing a silyl group from the reaction product.

Copper(I) salt is preferably used as a catalyst in the present reaction. Examples of the copper(I) salt can include copper halides such as copper(I) iodide and copper(I) bromide, but the types of the copper catalysts used are not limited thereto.

In the present reaction, in general, a palladium catalyst is preferably used. Examples of the palladium catalyst can include tetrakis(triphenylphosphine)palladium(0) and bis(triphenylphosphine)palladium(II) dichloride, but the types of the palladium catalysts used are not limited thereto.

In the present reaction, a base is preferably used. Examples of the base can include triethylamine, diisopropylethylamine, diethylamine, dicyclohexylamine and tert-butylamine, but the types of the bases used are not limited thereto.

In the present reaction, a solvent is preferably used. The type of a solvent used is not particularly limited, as long as it does not adversely affect the reaction. Examples of the solvent can include ethers such as tetrahydrofuran and 1,4-dioxane, and various solvents such as N,N-dimethylformamide, N,N-dimethylacetamide, N-methylpyrrolidone, dimethyl sulfoxide, toluene, benzene, acetonitrile, dichloromethane, 1,2-dichloroethane, chloroform and ethyl acetate, but the types of the solvents used are not limited thereto. In addition, the present reaction can also be carried out without using solvents.

Regarding the reaction temperature, the reaction can be carried out at a suitable temperature, depending on the reaction substrate and reagent used. The reaction can be carried out at a temperature from room temperature to 180° C., and more preferably at a temperature from 40° C. to 120° C.

Regarding the reaction time, the reaction can be carried out for a suitable period of time, depending on the reaction substrate and reagent used. The reaction time is preferably from 30 minutes to 6 hours.

The 2-halopyridine derivative (3) used in the present reaction can be synthesized according to a known method. In addition, instead of the 2-halopyridine derivative (3), a 2-(trifluoromethanesulfonyloxy)pyridine derivative, or 2-(substituted sulfonyloxy)pyridine derivatives such as a 2-(p-toluenesulfonyloxy)pyridine derivative and a 2-(methanesulfonyloxy)pyridine derivative, can also be used.

Examples of the mono-silyl protected acetylene that can be used in the present reaction can include trimethylsilylacetylene, triethylsilylacetylene, triisopropylsilylacetylene, tert-butyldimethylsilylacetylene and tert-butyldiphenylsilylacetylene, but are not limited thereto. Moreover, instead of the mono-silyl protected acetylene, appropriately protected mono protected acetylene can also be used. In this case, it is necessary that, after completion of the Sonogashira reaction, the used mono protected acetylene can be deprotected without damaging other structures and can be then used in the subsequent reaction.

In the subsequent deprotection reaction, publicly known reaction conditions can be applied depending on the type of the used mono-silyl protected acetylene or other mono protected acetylenes. For instance, the method described in Peter G. M. Wuts, Theodora W. Greene, Greene's Protecting Groups in Organic Synthesis, 4th edition, Wiley-Interscience, 2006, etc. can be applied. In the case of using the mono-silyl protected acetylene, tetra-n-butyl ammonium fluoride or the like can be used, for example. As a solvent, for example, ethers such as tetrahydrofuran can be used. In addition, additives such as water or acetic acid can also be added to the reaction system.

(A-2-3-3) Method for Producing Carboxylic Acid Compound (2) Using Amino Aldehyde Derivative (8) and Acetylene Derivative (9)

The present reaction can be carried out, for example, in the presence of silver(I) triflate and aniline. Reagents used herein and a combination thereof are not limited thereto.

Examples of the solvent that can be used in the present reaction can include dichloromethane, 1,2-dichloroethane and chloroform, but are not limited thereto.

Regarding the reaction temperature, the reaction can be carried out at a temperature from room temperature to 180° C., and more preferably at a temperature from 60° C. to 140° C.

Regarding the reaction time, the reaction can be carried out for a suitable period of time, depending on the reaction substrate and reagent used. The reaction time is preferably from 30 minutes to 6 hours.

Deprotection reaction of the carboxyl protecting group can be carried out by the same method as that described in the above (A-2-1).

(A-3) Condensation Reaction of Amine Compound (1) with Carboxylic Acid Compound (2)

Examples of a condensing reagent that can be used in the present reaction can include dicyclohexylcarbodiimide (DCC), 1-ethyl-3-(3-dimethylaminopropyl)carbodiimide (EDC) and the hydrochloride thereof, benzotriazol-1-yloxytris(dimethylamino)phosphonium hexafluorophosphate (BOP), (benzotriazol-1-yloxy)tripyrrolidinophosphonium hexafluorophosphate (PyBOP), O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), bis(2-oxo-3-oxazolidinyl)phosphinic chloride (BOP-Cl), 4-(4,6-dimethoxy-1,3,5-triazin-2-yl)-4-methylmorphonium chloride (DMT-MM), hexafluorophosphate {{[(1-cyano-2-ethoxy-2-oxoethylidene)amino]oxy}-4-morpholinomethylene}dimethylammonium hexafluorophosphate (COM U), propylphosphonic anhydride (T3P), N,N'-carbonyldiimidazole (CDI) and diphenylphosphoryl azide (DPPA), but are not limited thereto. The condensing reagent is preferably propylphosphonic anhydride (T3P).

In the case of using a condensing reagent such as dicyclohexylcarbodiimide (DCC), 1-ethyl-3-(3-dimethylaminopropyl)carbodiimide (EDC) or the hydrochloride thereof, 1-hydroxybenzotriazole (HOBt), 1-hydroxy-7-azabenzotriazole (HOAt) or the like may be added.

Moreover, it may also be possible to add a base, such as triethylamine, diisopropylethylamine, pyridine, 2,6-di-tert-butylpyridine, 2,6-lutidine, collidine, 2,6-di-tert-butyl-4-methylpyridine, 4-dimethylaminopyridine or imidazole, as necessary. However, the types of the bases used herein are not limited thereto.

Examples of a reaction solvent that can be used herein can include tetrahydrofuran, 1,4-dioxane, 1,2-dimethoxyethane, N,N-dimethylformamide, N,N-dimethylacetamide, N-methylpyrrolidone, acetonitrile, dichloromethane, 1,2-dichloroethane, chloroform and toluene, but are not limited thereto. The reaction solvent is preferably N,N-dimethylformamide, N,N-dimethylacetamide, or N-methylpyrrolidone.

Regarding the reaction temperature, the reaction can be carried out at a suitable temperature, depending on the reaction substrate and reagent used. The reaction can be carried out at a temperature from −20° C. to 120° C., and more preferably at a temperature from −5° C. to 70° C.

Regarding the reaction time, the reaction can be carried out for a suitable period of time, depending on the reaction substrate and reagent used. The reaction time is preferably from 30 minutes to 6 hours.

(A-4) Method for Synthesizing Compound (I), Using Intermediate Obtained by Converting Carboxylic Acid Compound (2) to Acid Halide The compound (I) can also be synthesized by leading the carboxylic acid compound (2) to an acid halide, and then condensing the acid halide with the amine (1). The acid halide can be isolated, as necessary. Examples of an acid halogenating reagent that can be used herein can include acid fluoride, acid chloride, and acid bromide.

Alternatively, the compound (I) can also be synthesized by leading the carboxylic acid (2) to a symmetric acid anhydride or a mixed acid anhydride, and then condensing it with the amine (1). The symmetric acid anhydride or the mixed acid anhydride can be isolated, as necessary. As such a mixed acid anhydride, a mixed acid anhydride obtained by reacting the carboxylic acid (2) with ethyl chloroformate, isobutyl chloroformate, tert-butyl chloroformate, pivalic acid chloride, etc. can be used.

Method B (B-1) The compound (I) can also be produced by forming an amide bond according to the condensation reaction of the amine compound (1) with a carboxylic acid compound (3B), and then performing a cross-coupling reaction.

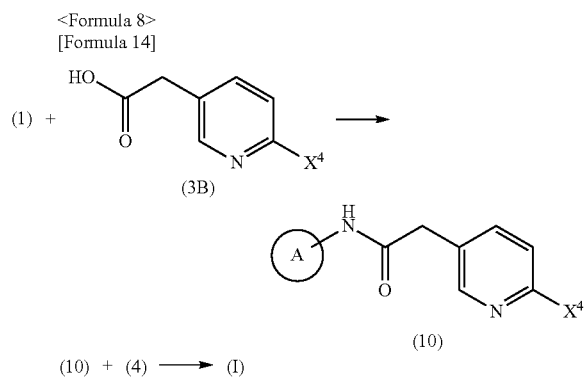

wherein $X^4$ represents a halogen atom.

In the condensation reaction and the cross-coupling reaction used herein, the same reaction conditions as those used in the above (A-2) can be applied.

In each of the above formulae, when $R^1$ and $R^2$ each represent a hydrogen atom, a raw material compound in which a nitrogen atom on a pyrazole ring is protected can be used. In such a case, after completion of the condensation reaction shown in formula 1, the protecting group is deprotected, so that the reaction product can be led to the compound (I). It is to be noted that protecting groups and the addition and removal reaction thereof can be carried out in accordance with Peter G. M. Wuts, Theodora W. Greene, Greene's Protecting Groups in Organic Synthesis, 4th edition, Wiley-Interscience, 2006, etc.

After completion of the reaction in each step as described above, a compound of interest is collected from the reaction mixture according to an ordinary method. For example, the reaction mixture is neutralized as appropriate, or when insoluble matters are present, such insoluble matters are removed by filtration, and water and an immiscible organic solvent such as ethyl acetate are then added to the residue, so that an organic layer containing a compound of interest is separated. Thereafter, the organic layer is washed with water or the like and is then dried over anhydrous sodium sulfate or the like, and the solvent is then distilled away to obtain the compound of interest. Moreover, the compound of interest can also be obtained by collecting insoluble matters generated in the reaction solution by filtration, or by adding water or an organic solvent to the reaction solution and then collecting the generated insoluble matters by filtration.

If necessary, the obtained product of interest can be separated and purified by appropriately combining ordinary methods, such as recrystallization or re-precipitation, or a method generally used in separation and purification of organic compounds, for example, a method of using synthetic adsorbents, such as adsorption column chromatography or partition column chromatography, a method of using ion exchange chromatography, or normal phase/reverse phase column chromatography of using silica gel or alkylated silica gel, and then eluting with an appropriate eluent.

Furthermore, an optically active body can be separated and/or purified using a chiral column, as necessary.

The RET kinase activity inhibiting effect and the RET kinase gatekeeper mutant activity inhibiting effect of the compound of the present invention can be measured by a kinase activity evaluation method that is generally used by a person skilled in the art. Such effects can be measured, for example, by a mobility shift assay method. Alternatively, the effects can also be measured by an alpha-LISA system, a Western blot method, or an ELISA method. Moreover, not only the RET kinase inhibiting effect, but also the inhibitory effect of the present compound on other kinases such as PDGFR, KIT, NTRK and FLT3, and the inhibitory effect of the present compound on KDR kinase associated with selectivity can also be measured by the same methods as described above.

The selectivity of the compound of the present invention to other kinases can also be confirmed by the above described mobility shift assay method, and the like. For example, a method that is based on the mobility shift assay method provided by Carna Biosciences, Inc. or a KinomeScan method provided by DiscoverX is applied to a kinase panel consisting of various types of kinases, so that the inhibitory activity of the compound on various types of kinases can be measured and kinase selectivity can be confirmed.

The RET kinase activity inhibiting effect, the RET kinase gatekeeper mutant activity inhibiting effect, and the KDR kinase activity inhibiting effect of the compound of the present invention, which are exhibited in cells, can be measured by a kinase activity evaluation method that is generally used by a person skilled in the art. For example, the effects can be measured by an alpha-LISA system, a Western blot method, or an ELISA method. Moreover, not only the inhibitory effect of the present compound on the RET and KDR kinases, but also the inhibitory effect on other kinases such as PDGFR, KIT, NTRK and FLt3 can be measured by the same methods as described above.

The growth inhibiting activity of the compound of the present invention on a non-small cell lung cancer cell line LC-2/ad and a thyroid gland cancer cell line TT can be measured using a growth inhibition test that is generally used by a person skilled in the art. For example, the activity can be measured by an ATP-Glo assay or an MTT assay. The growth inhibiting activity of the present compound on other cell lines can also be measured by the same methods as described above.

Moreover, the in vivo antitumor activity of the compound of the present invention can be examined using an antitumor test method that is generally used by a person skilled in the art. For example, as in the case of the aforementioned method, various types of tumor cells are transplanted into a mouse, a rat, and the like, and at the same time as the transplantation, or after the adhesion of the transplanted cells has been confirmed, the compound of the present invention is administered to the subject via oral administration, intravenous administration, etc. Several days to several weeks after the administration, the tumor growth in a drug non-administration group is compared with the tumor growth in a compound administration group, so that the in vivo antitumor activity of the present compound can be confirmed.

The water solubility of the compound of the present invention can be measured, for example, by adding to the present compound a medium to be examined, shaking the obtained mixture, leaving the reaction mixture for a while, filtering it, and measuring the concentration of the compound in the filtrate. As media used herein, buffer solutions having various pH values and media that imitate satiety or fasting intestinal juice can be used.

The penetration properties of the compound of the present invention to various tissues and/or organs, such as brain penetration, central penetration, and skin penetration, can be measured by administering the compound to various types of animals, excising the tissues or organs from the animals after a predetermined period of time has passed, appropriately treating them, measuring the concentration of the compound contained therein, and then comparing the measured concentration of the compound with the blood concentration thereof. There may be a case where the penetration properties can be more precisely measured, or can be noninvasively measured, by administering a fluorescence-labeled or radiolabeled compound to an animal.

The above described pyridine compound represented by general formula (I) of the present invention or a pharmaceutically acceptable salt can be used as a medicament containing the same, and preferably as an anticancer agent. Examples of the disease, for the treatment or prevention of which the compound of the present invention can be used, can include various types of cancer, sarcoma and leukemia, including: cancers such as adrenal cortex cancer, anus cancer, bile duct cancer, bladder cancer, breast cancer, uterine cervix cancer, colon cancer, endometrial cancer, esophageal cancer, Ewing's sarcoma, gallbladder cancer, hypopharyngeal cancer, pharyngeal cancer, lip and oral cancer, liver cancer, non-small cell lung cancer, melanoma, mesothelioma, multiple myeloma, ovary cancer, pancreatic cancer, prostate cancer, stomach cancer, testicular cancer, and thyroid gland cancer; leukemia such as chronic lymphocytic leukemia, acute lymphocytic leukemia, chronic myelogenous leukemia, and acute myelogenous leukemia; and lymphoma such as Hodgkin's lymphoma and non-Hodgkin's lymphoma.

The above described pyridine compound represented by general formula (I) of the present invention or a pharmaceutically acceptable salt is administered in various forms. The dosage form thereof is not particularly limited, and it is determined depending on various types of preparation forms, the age, sex and other conditions of a patient, the severity of a disease, and the like. For example, when the present compound or a pharmaceutically acceptable salt thereof is in the dosage form of tablet, pill, powder, granule, syrup, liquid, suspension, emulsion or capsule, it is orally administered. On the other hand, when the present compound or a pharmaceutically acceptable salt thereof is in a form of injection, it is intravenously administered, alone or by being mixed with an ordinary fluid replacement such as glucose or amino acid. Furthermore, such an injection is administered alone intramuscularly, intradermally, subcutaneously or intraperitoneally, as necessary. In the case of a suppository, it is rectally administered. The administration method is preferably oral administration.

Various types of these preparations can be formulated by adding known auxiliary agents that can be commonly used in the field of pharmaceutical preparations, such as an excipient, a binder, a disintegrator, a lubricant, a dissolving agent, a corrigent and a coating agent, to the main drug according to an ordinary method.

When the present compound or a pharmaceutically acceptable salt thereof is molded into a tablet, carriers that have been conventionally known in the present technical field can be widely used. Examples of the carrier can include: excipients such as lactose, saccharose, sodium chloride, glucose, urea, starch, calcium carbonate, kaolin, crystalline cellulose, and silicic acid; binders such as water, ethanol, propanol, simple syrup, glucose solution, starch solution, gelatin solution, carboxymethyl cellulose, Shellac, methyl cellulose, potassium phosphate, and polyvinyl pyrrolidone; disintegrators such as dry starch, sodium alginate, agar powder, laminarin powder, sodium hydrogen carbonate, calcium carbonate, polyoxyethylene sorbitan fatty acid esters, sodium lauryl sulfate, monoglyceride stearate, starch, and lactose; disintegration inhibitors such as saccharose, stearin, cacao butter, and hydrogenated oil; absorption promoters such as quaternary ammonium base and sodium lauryl sulfate; moisturizers such as glycerin and starch; adsorbents such as starch, lactose, kaolin, bentonite, and colloidal silicic acid; and lubricants such as purified talc, stearate, borax powder, and polyethylene glycol. In addition, the tablet can be further processed into a tablet that is coated with a general coating film, such as a sugar-coated tablet, a gelatin-coated tablet, an enteric-coated tablet, a film-coated tablet, or further, a double coated tablet or a multilayered tablet, as necessary.

When the present compound or a pharmaceutically acceptable salt thereof is molded into a pill, carriers that have been conventionally known in the present technical field can be widely used. Examples of the carrier can include: excipients such as glucose, lactose, starch, cacao butter, hydrogenated vegetable oil, kaolin, and talc; binders such as gum Arabic powder, tragacanth powder, gelatin, and ethanol; and disintegrators such as laminarin powder.

When the present compound or a pharmaceutically acceptable salt thereof is molded into a suppository, carriers that have been conventionally known in the present technical field can be widely used. Examples of the carrier can include polyethylene glycol, cacao butter, higher alcohol, higher alcohol esters, gelatin, and semi-synthetic glyceride.

When the present compound or a pharmaceutically acceptable salt thereof is prepared in the form of an injection agent, it is preferable that a liquid agent and a suspension agent be sterilized and be isotonic with the blood or the like. When the present compound or a salt thereof is molded into such a liquid agent, an emulsion, or a suspension agent, all of diluents that have been commonly used in the present technical field can be used. Examples of the diluent can include water, ethyl alcohol, propylene glycol, ethoxylated isostearyl alcohol, polyoxylated isostearyl alcohol, and polyoxyethylene sorbitan fatty acid esters. In this case, the pharmaceutical preparation may contain common salt, glucose or glycerin in an amount sufficient for preparation of an isotonic solution, and further, ordinary solubilizer, buffer, soothing agent and the like may also be added to the pharmaceutical preparation.

Still further, the pharmaceutical preparation may contain a coloring agent, a preservative, an aromatic, a flavor, a sweetener and the like, and other pharmaceutical products, as necessary.

The amount of the active ingredient compound contained in the above described pharmaceutical preparation is not particularly limited, and it is selected from a wide range, as appropriate. In general, it is adequate that the active ingredient compound is contained in an amount of 1% to 70% by weight, and preferably 1% to 30% by weight, based on the weight of the entire composition.

The dose differs depending on symptoms, age, body weight, administration method, dosage form, and the like. In general, the lower limit of the daily dose to an adult is 0.001 mg/kg (preferably 0.01 mg/kg, more preferably 0.1 mg/kg), and the upper limit thereof is 200 mg/kg (preferably 20 mg/kg, more preferably 10 mg/kg). The compound of the present invention can be administered at the above described dose, once or divided into several times per day.

The compound of the present invention can be used in combination with various therapeutic or preventive agents for the aforementioned diseases, for which the present invention is considered to be effective. For example, the compound of the present invention can be used in combination with, what is called, cancer chemotherapeutic agents such as alkylating agents (cyclophosphamide, bendamustine, temozolomide, mitomycin C, etc.), platinum preparations (cisplatin, carboplatin, etc.), antimetabolites (pemetrexed, 5-FU, capecitabine, etc.), tubulin inhibitors (vincristine, taxol, eribulin, etc.) and topoisomerase inhibitors (irinotecan, doxorubicin, etc.), and the preparations thereof having various forms. Moreover, the compound of the present invention can also be used in combination with various types of, what is called, biopharmaceutical products, including antibody preparations such as trastuzumab, bevacizumab and nivolumab, antibody-drug complexes such as T-DM1, etc. Furthermore, the present compound can also be used in combination with various types of, what is called, low-molecular-weight molecular-targeted agents, such as kinase inhibitors (imatinib, nilotinib, erlotinib, gefitinib, afatinib, osimertinib, sunitinib, dasatinib, ibrutinib, sorafenib, vemurafenib, trametinib, and palbociclib), proteasome inhibitors (bortezomib, etc.), HDAC inhibitors (vorinostat, etc.), and PARP inhibitors (olaparib, etc.). In addition to the aforementioned agents, the present compound can also be used in combination with immunomodulators such as thalidomide, interferons, and hormone therapy drugs (tamoxifen, anastrozole, etc.). Further, these agents are combined with one another, so that the present compound can be used in combination with three or more agents.

Advantageous Effects of Invention

According to the present invention, the compound represented by the above described formula (I) having RET kinase inhibiting activity is provided. Such a compound is useful as a therapeutic agent for a disease caused by the activating mutation or increased expression of RET kinase, a disease associated with the activating mutation or increased expression of RET kinase, and/or a disease attended with the activating mutation or increased expression of RET kinase, for example, as an anticancer agent.

DETAILED DESCRIPTION

Hereinafter, the present invention will be described in more detail in the following examples and the like. However, these examples are not intended to limit the scope of the present invention, and these examples are not restrictively interpreted in any sense. In addition, in the present description, the used reagents, solvents and starting materials are easily available from commercially available supply sources, unless otherwise specified.

The proton NMR was measured using a 400 MHz NMR spectrometer manufactured by JEOL, or a 400 MHz NMR spectrometer manufactured by Varian. The proton NMR spectral data show significant peaks, and the data are shown with a chemical shift (which is shown as relative ppm (δ) from a tetramethylsilane peak), the number of protons, and the multiplicity of peak splitting (which are shown as s: singlet; d: doublet; t: triplet; q: quartet; m: multiplet; br s: broad singlet; dd: doubled doublet, etc.), and further, the coupling constant is indicated as a J value (unit: Hz), if it can be explicitly described. The low-resolution mass spectral data are shown regarding the maximum ionization peak (corresponding to the maximum UV absorption peak in almost all cases) obtained after passing through a reverse phase high performance liquid chromatography column (Agilent System; column: Develosil Combi-RP-5, 2.0×50 mm, Cadenza CD-18, 3.0×75 mm, or ZORBAXSB-C18, 2.1×50 mm; solvent: 0.1% formic acid-containing acetonitrile/water system, or 0.01% trifluoroacetic acid-containing acetonitrile/water system), applying an electrospray ionization method (ESI) or an atmospheric pressure chemical ionization method (APCI).

The silica gel column chromatography was carried out applying a method of using a commercially available packed column and an automatic system (e.g., Biotage SP1 System, etc.), or a method comprising filling a glass-made column with Silica Gel 60 manufactured by Merck (particle diameter: 0.063-0.200 mm), and multiple types of solvents used were merely described. The amounts of solvents used, the ratio of the solvents, the timing of converting a solvent to another solvent, and a gradient method are not described herein. However, it is considered that the purification and/or separation methods applied herein can be easily reproduced with ordinary knowledge and/or technology in the field of chemical synthesis.

It is to be noted that the abbreviations used in the following examples have the following meanings.

mg: milligram, g: gram, mL: milliliter, and MHz: megahertz.

EXAMPLES

Example 1

Figure 1:
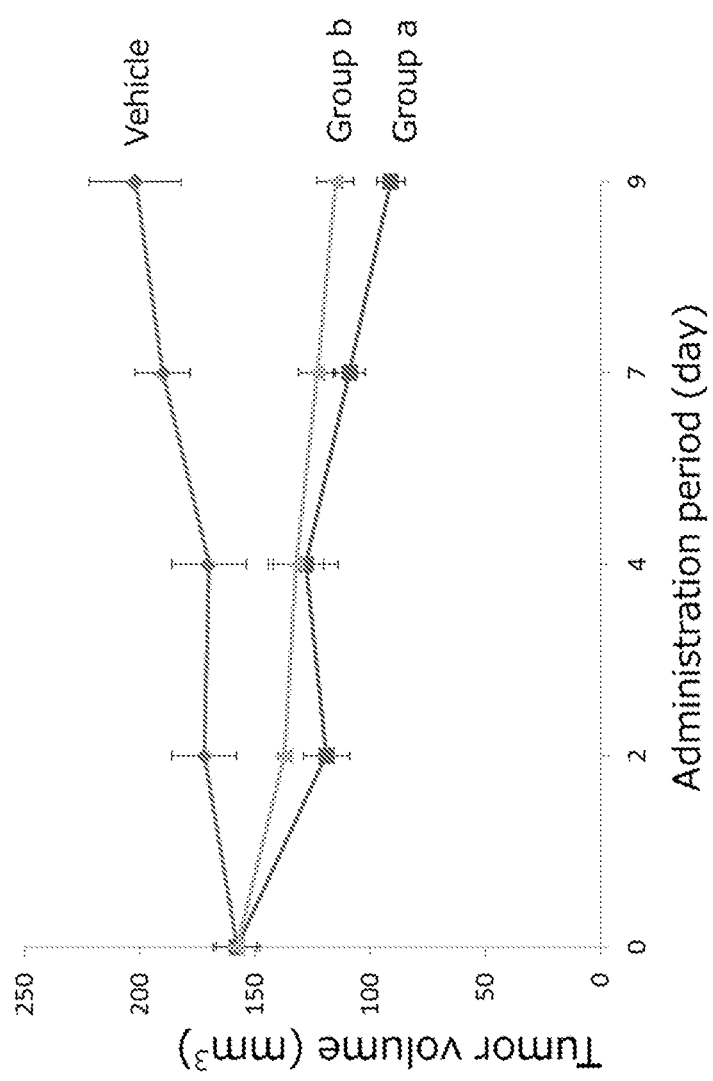
FIG. 1 shows the result of tumor regression effect in an antitumor activity test using a xenograft model established with a non-small cell lung cancer cell line LC-2/ad.

2-[6-(6,7-Dimethoxyquinolin-3-yl)pyridin-3-yl]-N-[5-(1,1,1-trifluoro-2-methylpropan-2-yl)-1,2-oxazol-3-yl]acetamide <1-1> (6,7-Dimethoxyquinolin-3-yl)boronic Acid Under the nitrogen atmosphere, a solution of 3-bromo-6,7-dimethoxyquinoline (17.03 g, 63.5 mmol) and triisopropyl borate (19.0 mL, 82.3 mmol) in tetrahydrofuran (170 mL) was cooled to −78° C., and a n-butyllithium hexane solution (1.60 mol/L, 58.0 mL, 92.8 mmol) was added dropwise to the solution over 1 hour. Thereafter, the mixed solution was stirred for 30 minutes at the same temperature as described above. Thereafter, the temperature of the reaction solution was increased to −30° C. to −40° C., 1 mol/L hydrochloric acid (170 mL) was slowly added to the reaction solution, and the temperature of the solution was then increased to room temperature. A 1 mol/L sodium hydroxide aqueous solution (50 mL) was added to the reaction solution, and the precipitated solid was collected by filtration. The obtained solid was dissolved in methanol, and then concentrated under reduced pressure. After that, a mixed solvent of chloroform/methanol (9:1) was added to the residue, and insoluble matters were then filtered off. An organic layer was separated from the obtained filtrate containing water, and a water layer was then saturated with sodium chloride, followed by extraction with a mixed solvent of chloroform/methanol (9:1) three times. The obtained organic layers were combined, and the combined layer was dried over anhydrous sodium sulfate, then filtrated, and then concentrated under reduced pressure to obtain the target compound (13.74 g, 59.0 mmol, yield: 72%) as an orange solid.

MS m/z: 234 (M+H)$^+$.

<1-2> Methyl [6-(6,7-dimethoxyquinolin-3-yl)pyridyl-3-yl]acetate

A solution of sodium carbonate (5.96 g, 56.2 mmol) in water (18 mL) was added to a suspension of (6,7-dimethoxyquinolin-3-yl)boronic acid (4.37 g, 18.75 mmol), methyl 2-(6-chloropyridyl-3-yl)acetate (3.47 g, 18.70 mmol) and 2-dicyclohexylphosphino-2',4',6'-triisopropylbiphenyl (895 mg, 1.88 mmol) in 1,4-dioxane (72 mL), followed by nitrogen substitution. Thereafter, tris(dibenzylideneacetone)dipalladium(0) (849 mg, 0.938 mmol) was added to the reaction mixture, and nitrogen substitution was then carried out again. The mixture was stirred at 80° C. for 3 hours. Subsequently, the reaction solution was cooled to room temperature, and a saturated sodium hydrogen carbonate aqueous solution (200 mL) was added to the reaction solution. The mixed solution was extracted with ethyl acetate three times, and the combined organic layer was then dried over anhydrous sodium sulfate. The resultant was concentrated under reduced pressure, and then purified by silica gel column chromatography (NH silica gel, ethyl acetate/hexane) to obtain the target compound (4.04 g, 12.46 mmol, yield: 67%) as a yellow solid.

$^1$H-NMR (CDCl$_3$) δ: 3.71 (2H, s), 3.74 (3H, s), 4.03 (3H, s), 4.06 (3H, s), 7.14 (1H, s), 7.46 (1H, s), 7.77 (1H, dd, J=8.2, 2.1 Hz), 7.84 (1H, d, J=7.3 Hz), 8.62 (1H, d, J=1.8 Hz), 8.64 (1H, d, J=1.8 Hz), 9.31 (1H, d, J=2.4 Hz).

MS m/z: 339 (M+H)$^+$.

<1-3> 2-[6-(6,7-Dimethoxyquinolin-3-yl)pyridyl-3-yl]acetic Acid

Tetrahydrofuran (20 mL), methanol (20 mL), and a 1 mol/L sodium hydroxide aqueous solution (20 mL, 20.0 mmol) were added to methyl 2-[6-(6,7-dimethoxyquinolin-3-yl)pyridin-3-yl]acetate (2.24 g, 6.91 mmol), and the obtained mixture was then stirred at room temperature for 1.5 hours. Thereafter, 1 mol/L hydrochloric acid (20 mL) was added to the reaction solution, and the mixed solution was then concentrated under reduced pressure. A mixed solvent of chloroform/methanol (9:1) was added to the obtained residue, followed by filtration. The obtained filtrate was concentrated under reduced pressure and then dried to obtain a roughly purified product of the target compound. The obtained roughly purified product was washed with diethyl ether, and then with a mixed solvent of ethanol/diethyl ether (1:1) to obtain the target compound (1.57 g, 4.83 mmol, yield: 70%) as a colorless solid.

$^1$H-NMR (DMSO-d$_6$): 3.69 (2H, s), 3.91 (3H, s), 3.93 (3H, s), 7.40 (1H, s), 7.45 (1H, s), 7.81 (1H, dd, J=8.2, 2.1 Hz), 8.06 (1H, d, J=8.5 Hz), 8.58 (1H, d, J=1.8 Hz), 8.81 (1H, d, J=1.8 Hz), 9.35 (1H, d, J=1.8 Hz).

MS m/z: 325 (M+H)$^+$.

<1-4>

2-[6-(6,7-Dimethoxyquinolin-3-yl)pyridin-3-yl]-N-[5-(1,1,1-trifluoro-2-methylpropan-2-yl)-1,2-oxazol-3-yl]acetamide Propylphosphonic anhydride (50% ethyl acetate solution, approximately 1.7 mol/L, 1.80 mL, 3.06 mmol) was added to a suspension of 2-[6-(6,7-dimethoxyquinolin-3-yl)pyridin-3-yl]acetic acid (486 mg, 1.495 mmol), 5-(1,1,1-trifluoro-2-methylpropan-2-yl)-1,2-oxazol-3-amine (320 mg, 1.648 mmol, described in J. Med. Chem., 2012, 55, 1082-1105) and pyridine (0.483 mL, 5.97 mmol) in N,N-dimethylformamide (12 mL), and the obtained mixture was then stirred at room temperature for 2 hours. Thereafter, the reaction mixture was poured into a mixture of water (90 mL) and a saturated sodium hydrogen carbonate aqueous solution (60 mL), and the obtained mixture was then cooled to 0° C. The precipitated solid was collected by filtration, and water and a saturated sodium hydrogen carbonate aqueous solution were then added to the obtained solid. The obtained solution was extracted with dichloromethane. The organic layer was dried over anhydrous sodium sulfate, and then concentrated under reduced pressure. The residue was purified by silica gel column chromatography (dichloromethane/methanol) to obtain the target compound (654 mg, 1.308 mmol, yield: 87%) as a colorless solid.

Example 2

2-[6-(6,7-Dimethoxyquinolin-3-yl)pyridin-3-yl]-N-[5-(1,1,1-trifluoro-2-methylpropan-2-yl)-1,2-oxazol-3-yl]acetamide Methanesulfonate A 2.0 mol/L methanesulfonic acid aqueous solution (0.821 mL, 1.642 mmol) was added to a suspension of 2-[6-(6,7-dimethoxyquinolin-3-yl)pyridin-3-yl]-N-[5-(1,1,1-trifluoro-2-methylpropan-2-yl)-1,2-oxazol-3-yl]acetamide (632 mg, 1.261 mmol) in isopropyl alcohol (12.6 mL) at room temperature, and the obtained mixture was then stirred for 30 minutes. Thereafter, the reaction mixture was cooled to 0° C., and then stirred for 1 hour. Thereafter, the generated solid was collected by filtration. The obtained solid was washed with isopropyl alcohol, and was then dried to obtain the target compound (734 mg, 1.230 mmol, yield: 98%) as a colorless solid.

Example 3

2-[6-(6,7-Dimethoxyquinolin-3-yl)pyridin-3-yl]-N-[3-(1,1,1-trifluoro-2-methylpropan-2-yl)-1,2-oxazol-5-yl]acetamide Propylphosphonic anhydride (50% ethyl acetate solution, approximately 1.7 mol/L, 1.80 mL, 3.06 mmol) was added to a suspension of the 2-[6-(6,7-dimethoxyquinolin-3-yl)pyridin-3-yl]acetic acid (486 mg, 1.495 mmol) obtained in Example 1-3, 3-(1,1,1-trifluoro-2-methylpropan-2-yl)-1,2-oxazol-5-amine (320 mg, 1.648 mmol, described in J. Med. Chem., 2012, 55, 1082-1105) and pyridine (0.483 mL, 5.97 mmol) in N,N-dimethylformamide (12 mL) at room temperature, and the obtained mixture was then stirred at the same temperature as described above for 2 hours. Thereafter, the reaction mixture was poured into a mixture of water (80 mL) and a saturated sodium hydrogen carbonate aqueous solution (80 mL), and the obtained mixture was then cooled to 0° C. The precipitated solid was collected by filtration, and thereafter, dichloromethane, water, and a saturated sodium hydrogen carbonate aqueous solution were successively added to the obtained solid, so that an organic layer was separated. The obtained organic layer was dried over anhydrous sodium sulfate, and then concentrated under reduced pressure. The residue was purified by silica gel column chromatography (dichloromethane/methanol) to obtain the target compound (683 mg, 1.366 mmol, yield: 91%) as a light yellow solid.

Example 4

2-[6-(6,7-Dimethoxyquinolin-3-yl)pyridin-3-yl]-N-[3-(1,1,1-trifluoro-2-methylpropan-2-yl)-1,2-oxazol-5-yl]acetamide Methanesulfonate A 2.0 mol/L methanesulfonic acid aqueous solution (0.883 mL, 1.766 mmol) was added to a suspension of 2-[6-(6,7-dimethoxyquinolin-3-yl)pyridin-3-yl]-N-[3-(1,1,1-trifluoro-2-methylpropan-2-yl)-1,2-oxazol-5-yl]acetamide (680 mg, 1.360 mmol) in isopropyl alcohol (20.4 mL) at room temperature, and the obtained mixture was then stirred at the same temperature as described above for 30 minutes. Thereafter, the reaction mixture was cooled to 0° C., and then stirred for 1 hour. The generated solid was collected by filtration. The obtained solid was washed with isopropyl alcohol, and then dried to obtain the target compound (626 mg, 1.050 mmol, yield: 77%) as a light yellow solid.

Example 5

2-[6-(6,7-Dimethoxyquinolin-3-yl)pyridin-3-yl]-N-[3-(1,1,1-trifluoro-2-methylpropan-2-yl)-1H-pyrazol-5-yl]acetamide <5-1> tert-Butyl 5-amino-3-(1,1,1-trifluoro-2-methylpropan-2-yl)-1H-pyrazole-1-carboxylate A solution of potassium hydroxide (7.0 g, 125 mmol) dissolved in water (15 mL) was added to a solution of 3-(1,1,1-trifluoro-2-methylpropan-2-yl)-1H-pyrazol-5-amine (2.6 g, 13.5 mmol, a compound synthesized by the second step of Example 42 in Section 155, WO 2014/141187) in dichloromethane (100 mL) at room temperature, and thereafter, the obtained mixture was intensively stirred at the same temperature as described above. To this reaction solution, di-tert-butyl dicarbonate (3.0 g, 13.8 mmol) was added at room temperature, and the thus obtained solution was stirred at the same temperature as described above for 4 hours. The separated organic layer was washed with a saturated saline, and then dried over sodium sulfate. Insoluble matters were removed by filtration, and the solvent was then distilled away under reduced pressure. The residue was purified by silica gel column chromatography (hexane/dichloromethane) to obtain the title compound (2.2 g, 7.5 mmol, yield: 56%) as a light yellow solid.

$^1$H-NMR (CDCl$_3$) δ: 1.49 (6H, s), 1.64 (9H, s), 5.15 (2H, brs), 5.46-5.47 (1H, m).

MS m/z: 194 (M+H-Boc)$^+$.

<5-2> tert-Butyl 5-({[6-(6,7-dimethoxyquinolin-3-yl)pyridin-3-yl]acetyl}amino)-3-(1,1,1-trifluoro-2-methylpropan-2-yl)-1H-pyrazole-1-carboxylate Propylphosphonic anhydride (50% ethyl acetate solution, approximately 1.7 mol/L, 46.0 mL, 78.2 mmol) was added to a solution of tert-butyl 5-amino-3-(1,1,1-trifluoro-2-methylpropan-2-yl)-1H-pyrazole-1-carboxylate (8.10 g, 27.6 mmol), the 2-[6-(6,7-dimethoxyquinolin-3-yl)pyridin-3-yl]acetic acid (8.5 g, 26.2 mmol) obtained in Example 1-2, and pyridine (21 mL, 261 mmol) in N,N-dimethylformamide (80 mL) at room temperature, and the obtained mixture was then stirred at the same temperature as described above for 5 hours. Thereafter, the reaction mixture was poured into a mixture of water (200 mL) and a saturated sodium hydrogen carbonate aqueous solution (100 mL), and the obtained mixture was then stirred at room temperature for 30 minutes. Thereafter, the precipitated solid was collected by filtration. The obtained solid was washed with water and then with hexane, and then dried under reduced pressure. The thus obtained crude product was suspended in diisopropyl ether (200 mL), and insoluble matters were then collected by filtration to obtain the target compound (15.21 g, 25.4 mmol, yield: 97%) as an almost colorless solid.

$^1$H-NMR (CDCl$_3$) δ: 1.51 (6H, s), 1.61 (9H, s), 3.83 (2H, s), 4.04 (3H, s), 4.07 (3H, s), 6.91 (1H, s), 7.16 (1H, s), 7.47 (1H, s), 7.83-7.90 (2H, m), 8.63 (1H, d, J=2.4 Hz), 8.70 (1H, d, J=1.8 Hz), 9.32 (1H, d, J=1.8 Hz), 10.34 (1H, s).

MS m/z: 600 (M+H)$^+$.

<5-3> 2-[6-(6,7-Dimethoxyquinolin-3-yl)pyridin-3-yl]-N-[3-(1,1,1-trifluoro-2-methylpropan-2-yl)-1H-pyrazol-5-yl]acetamide Trifluoroacetic acid (5.0 mL) was added to a solution of tert-butyl 5-({[6-(6,7-dimethoxyquinolin-3-yl)pyridin-3-yl]acetyl}amino)-3-(1,1,1-trifluoro-2-methylpropan-2-yl)-1H-pyrazole-1-carboxylate (0.81 g, 1.351 mmol) in dichloromethane (20 mL) under cooling on ice, and the temperature of the obtained mixture was then increased to room temperature, followed by stirring the mixture. The mixture was stirred at room temperature for 24 hours, and volatile components were then distilled away under reduced pressure. The residue was purified by silica gel column chromatography (NH silica gel, dichloromethane/ethyl acetate, and then dichloromethane/methanol). The obtained crude product was washed with a mixed solvent of ethyl acetate/hexane to obtain the title compound (0.64 g, 1.283 mmol, yield: 95%) as a light yellow solid.

Example 6

2-[6-(6,7-Dimethoxyquinolin-3-yl)pyridin-3-yl]-N-[3-(1,1,1-trifluoro-2-methylpropan-2-yl)-1H-pyrazol-5-yl]acetamide Methanesulfonate A 2.0 mol/L methanesulfonic acid aqueous solution (6.00 mL, 12.00 mmol) was added to a suspension of 2-[6-(6,7-dimethoxyquinolin-3-yl)pyridin-3-yl]-N-[3-(1,1,1-trifluoro-2-methylpropan-2-yl)-1H-pyrazol-5-yl]acetamide (4.00 g, 8.02 mmol) in isopropyl alcohol (80 mL) at room temperature, and the obtained mixture was then stirred at 60° C. until the reaction solution became a solution. Thereafter, the obtained solution was left at rest at room temperature overnight. The reaction solution, together with the precipitated solid, was stirred at room temperature for 4 hours, and the generated solid was collected by filtration. The obtained solid was dried under reduced pressure to obtain the target compound (4.14 g, 6.95 mmol, yield: 87%) as a light yellow solid.

Example 7

2-[6-(6,7-Dimethoxyquinolin-3-yl)pyridin-3-yl]-N-[1-methyl-3-(1,1,1-trifluoro-2-methylpropan-2-yl)-1H-pyrazol-5-yl]acetamide Propylphosphonic anhydride (50% ethyl acetate solution, approximately 1.7 mol/L, 0.18 mL, 0.306 mmol) was added to a solution of 1-methyl-3-(1,1,1-trifluoro-2-methylpropan-2-yl)-1H-pyrazol-5-amine (48 mg, 0.313 mmol, a compound synthesized by the second step of Example 41 in Section 153, WO 2014/141187), the 2-[6-(6,7-dimethoxyquinolin-3-yl)pyridin-3-yl]acetic acid (68 mg, 0.208 mmol) obtained in Example 1-3, and pyridine (0.050 mL, 0.618 mmol) in N,N-dimethylformamide (1 mL), and the obtained mixture was then stirred at 80° C. for 2.5 hours. The reaction solution was cooled to room temperature, and then stirred overnight. Thereafter, to the reaction solution, pyridine (0.017 mL, 0.210 mmol) and propylphosphonic anhydride (50% ethyl acetate solution, approximately 1.7 mol/L, 0.061 mL, and 0.104 mmol) were added, and the obtained mixture was then stirred at 80° C. for 2.5 hours. The reaction solution was cooled to room temperature, and a saturated sodium hydrogen carbonate aqueous solution (10 mL) was then added thereto. The mixed solution was extracted with ethyl acetate three times, and the obtained extracts were then combined. The combined extract was dried over anhydrous sodium sulfate, and then concentrated under reduced pressure. The residue was successively purified by silica gel column chromatography (methanol/dichloromethane), and then by silica gel column chromatography (NH silica gel, methanol/dichloromethane). The obtained crude product was suspended in diethyl ether, and a solid was then collected by filtration to obtain the target compound (48.9 mg, 0.095 mmol, yield: 46%) as a colorless solid.

Example 8

Alternative method for synthesizing methyl [6-(6,7-dimethoxyquinolin-3-yl)pyridyl-3-yl]acetate

<8-1> 2-Amino-4,5-dimethoxybenzaldehyde

A suspension of 4,5-dimethoxy-2-nitrobenzaldehyde (5.00 g, 23.7 mmol), 0.1 mol/L hydrochloric acid (10 mL), and 150 μm of iron powder (5.17 g, 92.6 mmol) in ethanol (70 mL) was stirred at 80° C. for 2.5 hours. Thereafter, the reaction solution was cooled to room temperature, and then filtrated through Celite (KANTO KAGAKU, Celite 545). The filtrate was concentrated under reduced pressure. Ethyl acetate was added to the residue, and the mixture was then filtrated through silica gel. The filtrate was concentrated under reduced pressure, and then dried to obtain the target compound (3.96 g, 21.9 mmol, yield: 92%) as a red solid.

$^1$H-NMR (CDCl$_3$) δ: 3.85 (3H, s), 3.89 (3H, s), 6.00-6.17 (3H, m), 6.88 (1H, s), 9.69 (1H, s).

MS m/z: 182 (M+H)$^+$.

<8-2> Methyl (6-{[tri(propan-2-yl)silyl]ethynyl}pyridin-3-yl)acetate

Nitrogen was bubbled into a suspension of copper(I) iodide (15.1 mg, 0.079 mmol), bis(triphenylphosphine)palladium(II) dichloride (58.0 mg, 0.083 mmol), methyl 2-(6-chloropyridin-3-yl)acetate (517 mg, 2.79 mmol), triethylamine (1.20 mL, 8.61 mmol), and triisopropylsilylacetylene (1.20 mL, 5.35 mol) in N,N-dimethylformamide (1 mL). Thereafter, the reaction system was substituted with nitrogen, and the suspension was then stirred at 80° C. for 5.5 hours. The reaction solution was cooled to room temperature, and water and a saturated saline were then added thereto, followed by extraction with ethyl acetate. The extract was dried over anhydrous sodium sulfate, and then concentrated under reduced pressure. The residue was purified by silica gel column chromatography (hexane/ethyl acetate) to obtain the target compound (888 mg, 2.55 mmol, yield: 92%) as a light yellow oily substance.

$^1$H-NMR (CDCl$_3$) δ: 1.06-1.18 (21H, m), 3.62 (2H, s), 3.69 (3H, s), 7.40-7.45 (1H, m), 7.54-7.61 (1H, m), 8.44-8.48 (1H, m).

MS m/z: 332 (M+H)$^+$.

<8-3> Methyl (6-ethynylpyridin-3-yl)acetate

Tetrabutylammonium fluoride (1 mol/L tetrahydrofuran solution, 17 mL) was added to a solution of methyl (6-{[tri(propan-2-yl)silyl]ethynyl}pyridin-3-yl)acetate (3.76 g, 10.82 mmol) and acetic acid (1 mL) in tetrahydrofuran (8.5 mL) at 0° C. under the nitrogen atmosphere, and the obtained mixture was then stirred for 5 minutes. The temperature of the reaction solution was increased to room temperature, and the solution was then stirred for 30 minutes. Thereafter, the reaction solution was concentrated under reduced pressure, and 3 mol/L hydrochloric acid (12 mL) was then added to the concentrate. The water phase was washed with hexane, and 5 mol/L sodium hydroxide (7 mL) was then added thereto, followed by extracting the mixture with ethyl acetate three times. The organic layers were combined, and the combined organic layer was dried over anhydrous sodium sulfate and then concentrated under reduced pressure. Ethyl acetate was added to the residue, and the obtained mixture was then filtrated through NH silica gel. The filtrate was concentrated under reduced pressure to obtain the target compound (1.83 g, 9.57 mmol, yield: 88%) as a brown solid.

$^1$H-NMR (CDCl$_3$) δ: 3.15 (1H, s), 3.65 (2H, s), 3.72 (3H, s), 7.43-7.49 (1H, m), 7.60-7.66 (1H, m), 8.47-8.52 (1H, m).

MS m/z: 176 (M+H)$^+$.

<8-4> Methyl [6-(6,7-dimethoxyquinolin-3-yl)pyridyl-3-yl]acetate

Aniline (0.110 mL, 1.207 mmol) was added to a suspension of methyl (6-ethynylpyridin-3-yl)acetate (103 mg, 0.539 mmol), 2-amino-4,5-dimethoxybenzaldehyde (130 mg, 0.715 mmol) and silver trifluoromethanesulfonate (29.4 mg, 0.114 mmol) in dichloroethane (1 mL), and the obtained mixture was then stirred under the nitrogen atmosphere at 80° C. for 2 hours. The reaction solution was cooled to room temperature, and then purified by silica gel column chromatography (ethyl acetate). Chloroform was added to the obtained roughly purified product, and insoluble matters were then removed by filtration. The filtrate was concentrated under reduced pressure to obtain the target compound (135 mg, 0.398 mmol, yield: 74%) as a green solid.

$^1$H-NMR (CDCl$_3$) δ: 3.72 (2H, s), 3.75 (3H, s), 4.04 (3H, s), 4.07 (3H, s), 7.16 (1H, s), 7.47 (1H, s), 7.75-7.82 (1H, m), 7.82-7.89 (1H, m), 8.59-8.68 (2H, m), 9.29-9.35 (1H, m).

MS m/z: 339 (M+H)$^+$.

The physical data of the compounds described in Examples 1 to 7 and the structures of the corresponding free form compounds will be shown below.

TABLE 1

| Ex. No. | Physical data | Structure |
|---|---|---|
| 1 | ¹H-NMR(CDCl₃) δ: 1.58 (6H, s), 3.84 (2H, s), 4.04 (3H, s), 4.07 (3H, s), 7.03 (1H, s), 7.16 (1H, s), 7.47 (1H, s), 7.81-7.88 (2H, m), 8.63 (1H, d, J = 1.8 Hz), 8.69 (1H, d, J = 1.2 Hz), 8.98 (1H, s), 9.31 (1H, d, J = 2.4 Hz). MS m/z: 501 (M + H)⁺. | (structure) |
| 2 | ¹H-NMR(CDCl₃) δ: 1.53 (6H, s), 3.07 (3H, s), 3.92 (2H, s), 4.12 (3H, s), 4.15 (3H, s), 6.94 (1H, s), 7.53 (1H, s), 7.76 (1H, s), 7.88 (2H, s), 8.49 (1H, s), 9.22 (1H, d, J = 1.8 Hz), 9.25 (1H, d, J = 1.8 Hz), 10.21 (1H, s). MS m/z: 501 (M + H − 96)⁺. | |
| 3 | ¹H-NMR(CDCl₃) δ: 1.55 (6H, s), 3.82 (2H, s), 4.04 (3H, s), 4.06 (3H, s), 6.52 (1H, s), 7.16 (1H, s), 7.46 (1H, s), 7.75-7.83 (2H, m), 8.56 (1H, d, J = 1.8 Hz), 8.61 (1H, d, J = 2.4 Hz), 9.19 (1H, d, J = 1.8 Hz), 9.70 (1H, s). MS m/z: 501 (M + H)⁺. | (structure) |
| 4 | ¹H-NMR(CDCl₃) δ: 1.47 (6H, s), 3.10 (3H, s), 3.94 (2H, s), 4.12 (3H, s), 4.14 (3H, s), 6.35 (1H, s), 7.46 (1H, s), 7.77-7.80 (2H, m), 7.88 (1H, dd, J = 7.9, 2.4 Hz), 8.52 (1H, d, J = 1.8 Hz), 9.13 (1H, d, J = 1.8 Hz), 9.29 (1H, d, J = 1.8 Hz), 11.18 (1H, s). MS m/z: 501 (M + H − 96)⁺. | |
| 5 | ¹H-NMR(DMSO-d₆) δ: 1.49 (6H, s), 3.74 (2H, s), 3.96 (3H, s), 3.94 (3H, s), 6.55 (1H, s), 7.42 (1H, s), 7.47 (1H, s), 7.87 (1H, dd, J = 8.5, 2.4 Hz), 8.10 (1H, d, J = 8.5 Hz), 8.65 (1H, d, J = 1.8 Hz), 8.83 (1H, d, J = 1.8 Hz), 9.37 (1H, d, J = 2.4 Hz), 10.81 (1H, s), 12.57 (1H, s). MS m/z: 500 (M + H)⁺. | (structure) |
| 6 | ¹H-NMR(DMSO-d₆) δ: 1.52 (6H, s), 3.05 (3H, s), 3.73 (2H, s), 4.12 (3H, s), 4.14 (3H, s), 6.52 (1H, s), 7.49-7.73 (4H, m), 8.32 (1H, s), 8.96 (1H, s), 9.21 (1H, d, J = 1.8 Hz), 10.48 (1H, s). MS m/z: 500 (M + H − 96)⁺. | |
| 7 | ¹H-NMR(DMSO-d₆) δ: 1.41 (6H, s), 3.66 (3H, s), 3.82 (2H, s), 3.92 (3H, s), 3.95 (3H, s), 6.28 (1H, s), 7.42 (1H, s), 7.49 (1H, s), 7.89 (1H, dd, J = 8.5, 2.4 Hz), 8.11 (1H, d, J = 8.5 Hz), 8.65 (1H, d, J = 1.8 Hz), 8.88 (1H, s), 9.38 (1H, d, J = 2.4 Hz), 10.31 (1H, s). MS m/z: 514 (M + H)⁺. | (structure) |

Reference Example 1

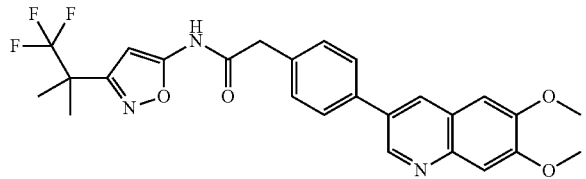 [SMILES: COc1cc2cc(-c3ccc(CC(=O)Nc4cc(C(C)(C)C(F)(F)F)no4)cc3)cnc2cc1OC]

<Step 1> Ethyl [4-(6,7-dimethoxyquinolin-3-yl)phenyl]acetate

To a solution of 3-bromo-6,7-dimethoxy-quinoline (2.0 g, 7.5 mmol), 4-(ethoxycarbonylmethyl)-phenylboronic acid pinacol ester (2.6 g, 9.0 mmol) and [1,1'-bis(diphenylphosphino)ferrocene]-palladium(II) dichloride dichloromethane adduct (0.61 g, 0.75 mmol) in 1,4-dioxane (36 mL) was added the solution of Sodium carbonate (2.4 g, 22 mmol) in water (4.0 mL) and the reaction mixture was stirred at 100° C. for 3 h. Reaction mixture was partitioned between water (0.15 L) and dichloromethane (2×0.15 L). The combined organic layer was washed with water (80 ml), followed by brine solution (30 ml). The organic layer was dried over anhydrous sodium sulphate, filtered and evaporated to dryness. The purification by flash column chromatography (dichloromethane/methanol) afforded ethyl 2-[4-(6,7-dimethoxy-3-quinolyl)phenyl]acetate (2.5 g, 7.0 mmol, 94% Yield) as light brown solid.

$^1$H-NMR (CDCl$_3$) δ: 1.29 (3H, t, J=7.2 Hz), 3.69 (2H, s), 4.04 (3H, s), 4.06 (3H, s), 4.19 (2H, q, J=7.2 Hz), 7.11 (1H, s), 7.43-7.44 (3H, m), 7.66 (2H, d, J=7.8 Hz), 8.15 (1H, d, J=2.0 Hz), 8.97 (1H, d, J=2.0 Hz).

MS m/z: 352 (M+H)$^+$.

<Step 2> [4-(6,7-Dimethoxyquinolin-3-yl)phenyl]acetic Acid

[4-(6,7-Dimethoxyquinolin-3-yl)phenyl]acetic acid was prepared as a yellow solid using a procedure analogous to that described in <Example 1-3>, substituting ethyl [4-(6,7-dimethoxyquinolin-3-yl)-phenyl]acetate for methyl [6-(6,7-dimethoxyquinolin-3-yl)pyridin-3-yl]acetate used in <Example 1-3>.

$^1$H-NMR (DMSO-D$_6$) δ: 3.65 (2H, s), 3.93 (3H, s), 3.95 (3H, s), 7.41-7.42 (4H, m), 7.77 (2H, d, J=8.3 Hz), 8.44 (1H, d, J=2.0 Hz), 9.01 (1H, d, J=2.0 Hz), 12.38 (1H, s). MS m/z: 324 (M+H)$^+$.

<Step 3> 2-[4-(6,7-Dimethoxyquinolin-3-yl)phenyl]-N-[3-(1,1,1-trifluoro-2-methylpropan-2-yl)-1,2-oxazol-5-yl]-acetamide 2-[4-(6,7-Dimethoxyquinolin-3-yl)phenyl]-N-[3-(1,1,1-trifluoro-2-methylpropan-2-yl)-1,2-oxazol-5-yl]-acetamide was obtained as a yellow solid using a procedure analogous to that described in <Example 3>, substituting [4-(6,7-dimethoxyquinolin-3-yl)phenyl]acetic acid for [6-(6,7-dimethoxyquinolin-3-yl)-pyridin-3-yl]acetic acid used in <Example 3>.

$^1$H-NMR (CDCl$_3$) δ: 1.54 (6H, s), 3.86 (2H, s), 4.05 (3H, s), 4.07 (3H, s), 6.49 (1H, s), 7.12 (1H, s), 7.44-7.46 (3H, m), 7.72-7.74 (2H, m), 8.11 (1H, s), 8.17 (1H, d, J=2.4 Hz), 8.95 (1H, d, J=2.4 Hz). MS m/z: 500 (M+H)$^+$.

<Step 4> 2-[4-(6,7-Dimethoxyquinolin-3-yl)phenyl]-N-[3-(1,1,1-trifluoro-2-methylpropan-2-yl)-1,2-oxazol-5-yl]-acetamide Mesylate 2-[4-(6,7-Dimethoxyquinolin-3-yl)phenyl]-N-[3-(1,1,1-trifluoro-2-methylpropan-2-yl)-1,2-oxazol-5-yl]-acetamide mesylate was prepared using a procedure analogous to that described in <Example 4>, substituting 2-[4-(6,7-dimethoxyquinolin-3-yl)phenyl]-N-[3-(1,1,1-trifluoro-2-methylpropan-2-yl) 1,2-oxazol-5-yl]acetamide for 2-[6-(6,7-dimethoxyquinolin-3-yl)pyridin-3-yl]-N-[3-(1,1,1-trifluoro-2-methylpropan-2-yl)-1,2-oxazol-5-yl]acetamide used in <Example 4>

$^1$H-NMR (CDCl$_3$) δ: 1.49 (6H, s), 3.05 (3H, s), 3.88 (2H, s), 4.11 (3H, s), 4.16 (3H, s), 6.41 (1H, s), 7.35 (1H, s), 7.49 (2H, d, J=7.8 Hz), 7.55 (2H, d, J=7.8 Hz), 7.90 (1H, s), 8.71 (1H, s), 8.92 (1H, s), 9.78 (1H, s). MS m/z: 500 (M+H-96)$^+$.

Reference Example 2

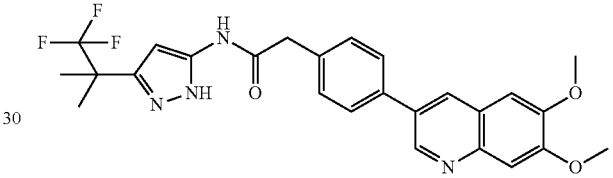

<Step 1> tert-Butyl 5-({[4-(6,7-dimethoxyquinolin-3-yl)phenyl]acetyl}amino)-3-(1,1,1-trifluoro-2-methylpropan-2-yl)-1H-pyrazole-1-carboxylate tert-Butyl 5-({[4-(6,7-dimethoxyquinolin-3-yl)phenyl]acetyl}amino)-3-(1,1,1-trifluoro-2-methylpropan-2-yl)-1H-pyrazole-1-carboxylate was obtained as a colorless solid using a procedure analogous to that described in <Example 5-2>, substituting [4-(6,7-dimethoxyquinolin-3-yl)phenyl]acetic acid for [6-(6,7-dimethoxy-quinolin-3-yl)pyridin-3-yl]acetic acid used in <Example 5-2>.

$^1$H-NMR (CDCl$_3$) δ: 1.51 (6H, s), 1.59 (9H, s), 3.83 (2H, s), 4.05 (3H, s), 4.07 (3H, s), 6.92 (1H, s), 7.11 (1H, s), 7.46-7.49 (3H, m), 7.70-7.72 (2H, m), 8.16 (1H, d, J=1.8 Hz), 8.97 (1H, d, J=2.4 Hz), 10.23 (1H, s). MS m/z: 599 (M+H)$^+$.

<Step 2> 2-[4-(6,7-Dimethoxyquinolin-3-yl)phenyl]-N-[3-(1,1,1-trifluoro-2-methylpropan-2-yl)-1H-pyrazol-5-yl]-acetamide 2-[4-(6,7-Dimethoxyquinolin-3-yl)phenyl]-N-[3-(1,1,1-trifluoro-2-methylpropan-2-yl)-1H-pyrazol-5-yl]-acetamide was prepared as a colorless solid using a procedure analogous to that described in <Example 5-3>, substituting tert-butyl 5-({[4-(6,7-dimethoxyquinolin-3-yl)phenyl]acetyl}amino)-3-(1,1,1-trifluoro-2-methylpropan-2-yl)-1H-pyrazole-1-carboxylate for tert-butyl 5-({[6-(6,7-dimethoxyquinolin-3-yl)pyridin-3-yl]acetyl}amino)-3-(1,1,1-trifluoro-2-methylpropan-2-yl)-1H-pyrazole-1-carboxylate used in <Example 5-3>.

$^1$H-NMR (CDCl$_3$) δ: 1.53 (6H, s), 3.81 (2H, s), 4.05 (3H, s), 4.06 (3H, s), 6.47 (1H, br s), 7.12 (1H, s), 7.25-7.29 (1H, m), 7.43-7.46 (3H, m), 7.69 (2H, d, J=7.9 Hz), 7.93 (1H, s), 8.15 (1H, s), 8.94 (1H, s). MS m/z: 499 (M+H)⁺.

Reference Example 3

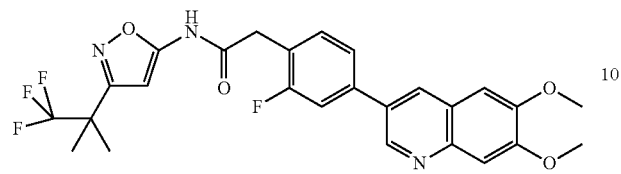

<Step 1> Methyl (4-bromo-2-fluorophenyl)acetate

To a stirring solution of 4-bromo-2-fluorophenylacetic acid (2.5 g, 11 mmol) and potassium carbonate (4.5 g, 32 mmol) in N,N-dimethylformamide (30 mL) was added iodomethane (0.80 mL, 13 mmol) at 0° C. and reaction mixture was allowed to stir at room temperature for 1 h. Reaction mixture was left overnight. Stirring at room temperature was resumed for another 1 h. Reaction mixture was partitioned between aqueous saturated solution of NaHCO₃ (150 mL) and ethyl acetate (2×100 mL). The combined ethyl acetate layer was washed with water (60 ml), followed by brine solution (30 ml). The organic layer was dried over anhydrous sodium sulphate, filtered and evaporated to dryness to afford methyl (4-bromo-2-fluorophenyl)acetate (2.5 g, 10 mmol, 96% Yield) as a colorless liquid.

¹H-NMR (CDCl₃) δ: 3.63 (2H, s), 3.71 (3H, s), 7.14-7.15 (1H, m), 7.24-7.25 (1H, m), 7.27-7.27 (1H, m).

<Step 2> Methyl [4-(6,7-dimethoxyquinolin-3-yl)-2-fluorophenyl]acetate

A solution of methyl 2-(4-bromo-2-fluoro-phenyl)acetate (0.58 g, 2.3 mmol), bis(pinacolato)diboron (0.65 g, 2.6 mmol), [1,1'-bis(diphenylphosphino)ferrocene]palladium (II) dichloride dichloromethane adduct (0.19 g, 0.23 mmol) and potassium acetate (0.69 g, 7.0 mmol) in 1,4-dioxane (8.0 mL) was heated at 100° C. for 1 h. To this resulting mixture was added 3-bromo-6,7-dimethoxy-quinoline (0.50 g., 1.9 mmol) and sodium carbonate (0.74 g, 7.0 mmol) dissolved in water (2.0 mL) and stirring at 100° C. was continued for 3 h. Reaction mixture was partitioned between water (70 mL) and dichloromethane (2×70 mL). The combined organic layer was washed with water (40 mL), followed by brine solution (20 mL). The organic layer was dried over anhydrous sodium sulphate, filtered and evaporated to dryness. The purification by flash column chromatography (dichloromethane/methanol) afforded I methyl 2-[4-(6,7-dimethoxy-3-quinolyl)-2-fluoro-phenyl]acetate (0.64 g, 1.8 mmol) as a right brown solid.

¹H-NMR (CDCl₃) δ: 3.74-3.76 (5H, m), 4.05 (3H, s), 4.06 (3H, s), 7.11 (1H, s), 7.40-7.44 (4H, m), 8.14 (1H, d, J=2.0 Hz), 8.95 (1H, d, J=2.0 Hz). MS m/z: 356 (M+H)⁺.

<Step 3> [4-(6,7-Dimethoxyquinolin-3-yl)-2-fluorophenyl]acetic Acid

[4-(6,7-Dimethoxyquinolin-3-yl)-2-fluorophenyl]acetic acid was obtained as a yellow solid using a procedure analogous to that described in <Example 1-3>, substituting methyl [4-(6,7-dimethoxyquinolin-3-yl)-2-fluorophenyl]ac- etate for methyl [6-(6,7-dimethoxyquinolin-3-yl)pyridin-3-yl]acetate used in <Example 1-3>.

¹H-NMR (DMSO-D₆) δ: 3.70 (2H, s), 3.93 (3H, s), 3.96 (3H, s), 7.40-7.41 (2H, m), 7.49 (1H, t, J=8.1 Hz), 7.64-7.65 (1H, m), 7.68-7.70 (1H, m), 8.51 (1H, s), 9.04 (1H, d, J=2.0 Hz), 12.52 (1H, s). MS m/z: 342 (M+H)⁺.

<Step 4> 2-[4-(6,7-Dimethoxyquinolin-3-yl)-2-fluorophenyl]-N-[3-(1,1,1-trifluoro-2-methylpropan-2-yl)-1,2-oxazol-5-yl]acetamide 2-[4-(6,7-Dimethoxyquinolin-3-yl)-2-fluorophenyl]-N-[3-(1,1,1-trifluoro-2-methylpropan-2-yl)-1,2-oxazol-5-yl] acetamide was prepared as a yellow solid using a procedure analogous to that described in <Example 3>, substituting [4-(6,7-dimethoxyquinolin-3-yl)-2-fluorophenyl]acetic acid for [6-(6,7-dimethoxyquinolin-3-yl)pyridin-3-yl]acetic acid used in <Example 3>.

¹H-NMR (CDCl₃) δ: 1.54 (6H, s), 3.87 (2H, s), 4.05 (3H, s), 4.07 (3H, s), 6.49 (1H, s), 7.12 (1H, s), 7.46-7.47 (3H, m), 7.51-7.52 (1H, m), 8.15 (1H, d, J=2.4 Hz), 8.34 (1H, s), 8.93 (1H, d, J=2.4 Hz). MS m/z: 518 (M+H)⁺.

Test Examples

<Test Example 1> Evaluation of RET Kinase Inhibiting Activity (Cell-Free System)

A reaction buffer (100 mM HEPES (pH 7.4), 10 mM MgCl₂, 0.003% Brij-35, 0.004% Tween-20, and 1 mM DTT) was mixed with a RET recombinant protein (RET—wild type; Invitrogen # PV3819, final concentration: 80 pg/ul, or a RET—Gatekeeper mutation (V804L); Invitrogen # PV4397, final concentration: 80 pg/ul) to prepare a RET kinase solution. The test compound was prepared to have a final concentration of 4000 nm with DMSO, and further, test compound samples at 12 different concentrations were prepared with a dilution magnification of √10. 19 uL of the RET kinase solution was added to each of lines A to P of a 384-well plate, and thereafter, the test compound at each concentration was added to lines C to N, and further, 1 uL of dimethyl sulfoxide (hereinafter referred to as DMSO) was added to each of lines A, B, O and P. Thereafter, the obtained mixtures were each preincubated at room temperature for 20 minutes. Furthermore, a substrate solution A containing ATP (final concentration: 1 mM) and a substrate solution B containing no ATP, both in addition to a reaction buffer and FL-Peptide 22 (PerkinElmer, #760366, final concentration: 1.5 uM) were produced. The substrate solution A was added in an amount of 5 uL to lines B to 0, whereas the substrate solution B was added in an amount of 5 uL to lines A and P. The obtained mixtures were each incubated at 28° C. for 45 minutes. A reaction termination solution (100 mM HEPES (pH 7.4), 0.015% Briji-35, 40 mM EDTA, and 0.1% Coating Reagent 3) was added in an amount of 40 ul to the reaction mixture, so as to terminate the reaction.

Using EZ Reader II (Perkin Elmer), a substrate peptide was separated from a phosphorylated peptide in the reaction solution, and the product ratio (P/(P+S)) calculated from the peak (S) of the substrate peptide and the peak (P) of the phosphorylated peptide was used for evaluation. The inhibition of the test compound having each concentration was obtained by the following formula (automatically calculated using the software of EZ Reader II System).

Inhibition (%)=100×(1−$C_t$/$C_o$)     (a)

$C_i$: Conversion rate of a reaction of a test compound with substrate solution A−conversion rate of a reaction of DMSO with substrate solution B $C_o$: Conversion rate of a reaction of DMSO with substrate solution A−conversion rate of a reaction of DMSO with substrate solution B Based on the inhibition rates of the test compound at 12 different concentrations according to the formula (a), a 4-parameter logistic regression curve was drawn. At this time, the 4-parameter logistic regression equation is expressed as follows.

$$\text{Inhibition (\%)} = \text{Bottom} + (\text{Top} - \text{Bottom})/(1 + (X/IC50)^{-slope}) \quad (b)$$

Top: Upward asymptote
Slope: Slope parameter
IC50: Value X of (Top+Bottom)/2
Bottom: Downward asymptote
X: Concentration of test compound First, any given initial values are inputted into Top, Slope, IC50, Bottom (Top=100, Slope=−1, IC50=approx. IC50, and Bottom=0), so that a regression curve was drawn. Subsequently, a least-squares method was executed to the sum of squares of a difference between the measured value and the estimated value obtained from formula (b) to calculate the coefficient of the 4-parameter logistic regression equation, so as to calculate IC50.

TABLE 2

| Ex. No. | RET-wild type IC50 (nM) | RET-V804L IC50 (nM) |
|---|---|---|
| 3 | 4.6 | 6.3 |
| 5 | 2.2 | 2.7 |
| Alectinib* | 52 | 811 |

*Alectinib: 9-Ethyl-6,6-dimethyl-8-[4-(morpholin-4-yl)piperidin-1-yl]-11-oxo-6,11-dihydro-5H-benzo[b]carbazole-3-carbonitrile <Test Example 2> Evaluation of KDR Kinase Inhibiting Activity (Cell System)

HUVEC cells were seeded on a plate at a cell density of 1500 cells per well, and then cultured overnight. The test compound (10 uM, 2.5 uM, 625 nM, 156 nM, 50 nM, 10 nM, 2.5 nM, or 0.6 nM) was added to each well, followed by culturing the obtained mixture for 2 hours. Thereafter, VEGF165 (Peprotech, #100-20) was added to the culture at a final concentration of 50 ng/ml, and the obtained mixture was then reacted at 37° C. for 5 minutes. Thereafter, the resulting cells were lysed with 50 ul of Lysis buffer included in AlphaLISA SureFire Ultra (Perkin Elmer, # ALSU-PVGFR-A500), and Acceptor beads and Donor beads were then added to 10 ul of the cell lysate according to the instruction manual included with the aforementioned kit. The mixture thus obtained was reacted at room temperature overnight, and thereafter, a KDR kinase inhibiting activity rate was measured using Envision (Perkin Elmer).

The value for a well to which only the Lysis buffer had been added was subtracted as a background from all of the values. Thereafter, the value for a well to which VEGFR had been added and the test compound had not been added was defined as a KDR kinase activity of 100%, and the obtained value was corrected. Using the Growth function of Microsoft Excel 2010, the 50% inhibition value of each test compound was estimated, and it was used as a value of IC50.

TABLE 3

| Ex. No. | IC50 (nM) |
|---|---|
| 4 | 298 |
| 6 | 566 |

<Test Example 3> Evaluation of RET Kinase Inhibiting Activity (Cell System)

Ba/F3 cells in which a Myc tagged RET gene or a RET (V804L) mutant gene had been overexpressed were seeded on a plate at a cell density of 500,000 cells per well, and the test compound (10 uM, 2.5 uM, 625 nM, 156 nM, 50 nM, 10 nM, 2.5 nM, or 0.6 nM) was then added to each well, followed by culturing the obtained mixture for 2 hours. Thereafter, 1 mL of Cell Lysis Buffer (Cell signaling technology, #9803), a single tablet of Phosphatase inhibitor (Roche, #04906837001), and a single tablet of Protease inhibitor (Roche, #0469312400) were added to 9 mL of MilliQ, and 20 ul of the obtained mixture was then added to each well. The mixture thus obtained was placed on ice for 20 minutes, so that the cells were lysed. A 5-ul aliquot was taken from the cell lysate, and thereafter, 64 nl of Myc antibody (Cell signaling technology, #3946) and Streptavidin Donor beads in an equal amount of 102 nl of P-Tyr-100 Acceptor beads included in the Alpha Screen Phosphotyrosine (P-Tyr-100) assay kit (Perkin Elmer, #6760620C) were added to the aliquot in accordance with the instruction manual included with the aforementioned assay kit. The obtained mixture was reacted at room temperature overnight, and a RET kinase inhibiting activity rate was then measured using Envision.

From all of the values, the value of a well, to which only the Lysis buffer had been added, was subtracted as a background value, and thereafter, the obtained value was then corrected, while defining the value of a well, to which the test compound had not been added, as a RET kinase activity of 100%. Using the Growth function of Microsoft Excel 2010, the 50% inhibition value of each test compound was estimated, and it was used as a value of IC50.

TABLE 4

| Ex. No. | RET-wild type IC50 (nM) | RET-V804L IC50 (nM) |
|---|---|---|
| 3 | 4 | 15 |
| 5 | 10 | 15 |
| Alectinib* | 161 | 2141 |

*Alectinib: 9-Ethyl-6,6-dimethyl-8-[4-(morpholin-4-yl)piperidin-1-yl]-11-oxo-6,11-dihydro-5H-benzo[b]carbazole-3-carbonitrile <Test Example 4> Measurement of Cell Growth Inhibitory Activity Using Non-Small Cell Lung Cancer Cell Line LC-2/ad The cell growth inhibitory activity of the test compound on the non-small cell lung cancer cell line LC-2/ad having a CCDC6-RET fusion gene (RIKEN, J Thorac Oncol. 2012 December, 7(12), 1872-6) was measured.

LC-2/ad cells were seeded on a 96-well plate at a cell density of 5,000 cells per well, and then cultured at 37° C. in the presence of 5% $CO_2$ overnight in a medium prepared by mixing RPMI-1640 containing 15% FBS and 25 mM HEPES with Ham's F12 Mixture at a mixing ratio of 1:1. Thereafter, the test compound was diluted, and then added to the 96-well plate. As a negative control, dimethyl sulfoxide (hereinafter referred to as DMSO) was added. The obtained mixture was cultured at 37° C. in the presence of 5% $CO_2$ for 9 days, and thereafter, a cell count measuring reagent CellTiter-Glo® Luminescent Cell Viability Assay (Promega, # G7571) was added to the culture, followed by stirring the mixture. Thereafter, using a luminescence measurement device Envision, the luminescence intensity was measured. The measurement value of a well to which only the medium had been added was define as a survival rate of 0%, and the measurement value of a well to which DMSO had been added was defined as a survival rate of 100%. The survival rate of the LC-2/ad cells in the presence of each concentration of the test compound was calculated. Using the Growth function of Microsoft Excel 2010, the 50% inhibition value of each test compound was estimated, and it was used as a value of IC50.

TABLE 5

| Ex. No. | IC50 (nM) |
| --- | --- |
| 4 | 49 |
| 5 | 82 |
| Alectinib* | 308 |

*Alectinib: 9-Ethyl-6,6-dimethyl-8-[4-(morpholin-4-yl)piperidin-1-yl]-11-oxo-6,11-dihydro-5H-benzo[b]carbazole-3-carbonitrile <Test Example 5> Measurement of Cell Growth Inhibitory Activity Using Thyroid Gland Cancer Cell Line TT The cell growth inhibitory activity of the test compound on the thyroid gland cancer cell line TT having RET activating mutation (C634W) (Biochemical and Biophysical Research Communications. 1995 Feb. 27 (207), 1022-1028) was measured.

TT cells were seeded on a 96-well plate at a cell density of 5,000 cells per well, and were then cultured at 37° C. in the presence of 5% $CO_2$ overnight in an F-12K nutrient mixture medium containing 10% FBS. Thereafter, the compound was diluted, and then added to the 96-well plate. As a negative control, dimethyl sulfoxide (hereinafter referred to as DMSO) was added. The obtained mixture was cultured at 37° C. in the presence of 5% $CO_2$ for 9 days, and thereafter, a cell count measuring reagent CellTiter-Glo® Luminescent Cell Viability Assay was added to the culture, followed by stirring the mixture. Thereafter, using a luminescence measurement device Envision (Perkin Elmer), the luminescence intensity was measured. The measurement value of a well to which only the medium had been added was define as a survival rate of 0%, and the measurement value of a well to which DMSO had been added was defined as a survival rate of 100%. The survival rate of the TT cells in the presence of each concentration of the test compound was calculated. Using the Growth function of Microsoft Excel 2010, the 50% inhibition value of each test compound was estimated, and it was used as a value of IC50.

TABLE 6

| Ex. No. | IC50 (nM) |
| --- | --- |
| 4 | 6 |
| 5 | 17 |
| Alectinib* | 112 |

Figure 2:
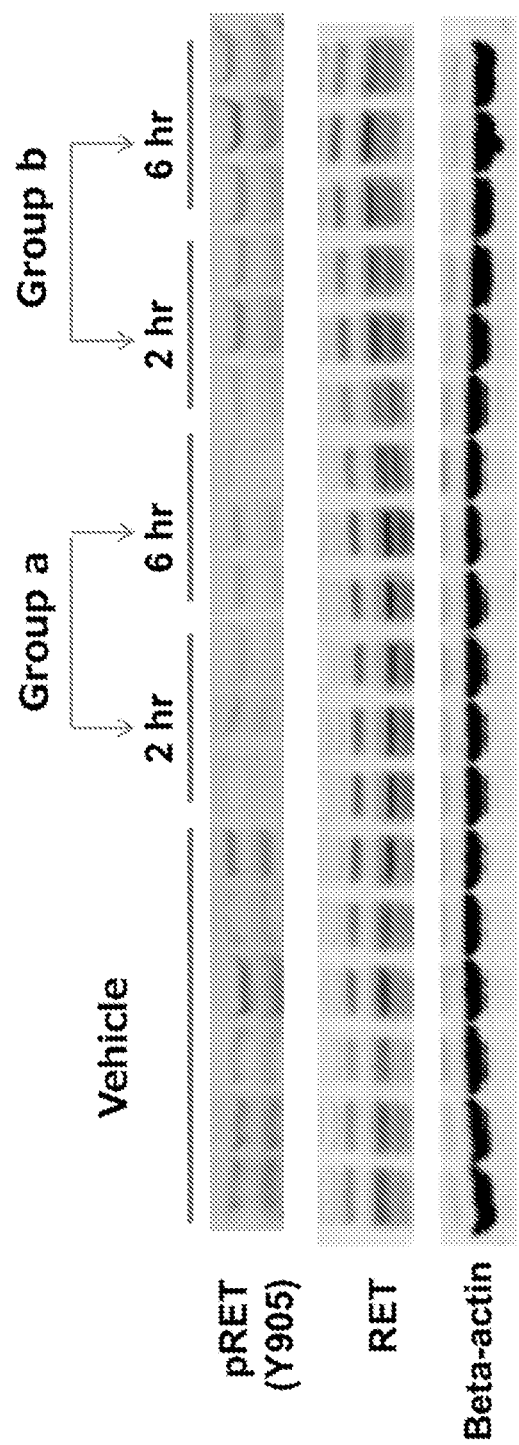
FIG. 2 shows the result of decreasing effect for RET phosphorylation of the tyrosine at position 905, which is used as an indicator of RET kinase activity.

*) Alectinib: 9-Ethyl-6,6-dimethyl-8-[4-(morpholin-4-yl)piperidin-1-yl]-11-oxo-6,11-dihydro-5H-benzo[b]carbazole-3-carbonitrile <Test Example 6> Evaluation of Antitumor Activity Using a Xenograft Model Established with Non-Small Cell Lung Cancer Cell Line LC-2/ad Cells of a non-small cell lung cancer cell line LC-2/ad (RIKEN, J Thorac Oncol. 2012 December, 7(12), 1872-6) suspended in DPBS (Gibco, #14190) were mixed with an equal amount of Corning Matrigel Basement Membrane Matrix (Corning, #354234), and the obtained mixture was then subcutaneously transplanted into NOG mice to form a tumor. (The NOG mice were acclimatized after they had been received from In Vivo Science Inc., and thereafter, the cells were transplanted into the mice when the mice were 9 week olds. As feedstuff, FR-2 (manufactured by Funabashi Farm Co., Ltd.) was used.) After the tumor had reached a size of 100 to 200 $mm^3$, the mice were randomized based on tumor diameter, and oral administration of the compound of Example 4 (hereinafter referred to as Compound A) was then initiated. As a solvent for dissolving Compound A, 1% hydroxypropyl methyl cellulose was used. Oral administration of Compound A at a dose of 3 mg/kg or 1 mg/kg per body weight of mouse three times a day was continued for 9 days [wherein a group to which 3 mg/kg Compound A was administered three times a day is referred to as an administration group a (■), a group to which 1 mg/kg Compound A was administered three times a day is referred to as an administration group b (▲), and a group to which only solvent was administered is referred to as a Vehicle group (♦)]. As a result, a dose-dependent tumor regression was observed (FIG. 1). During this test, no significant reduction in body weight was observed in the compound A administration groups as compared to the Vehicle group. Moreover, the tumor was collected (no administration was carried out on the Vehicle group) two hours and six hours after the final administration of Compound A, and the RET phosphorylation of the tyrosine at position 905 used as an indicator of RET kinase activity (pRET(Y905), Nature Medicine, 18, 375-377 (2012)) was then detected by the Western blotting method. As a result, dose-dependent suppression of the phosphorylation of Y905 was confirmed (FIG. 2).

[Comparative Data 1]

RET $IC_{50}$ and KDR $IC_{50}$ values (cell system) of compounds of the invention (Table 7) and comparator compounds (Table 8) are provided below. It is evident from Table 8 that the comparator compounds are equipotent at RET and KDR. In contrast, Table 7 shows that the compounds of the invention are selective for RET over KDR.

TABLE 7

| Ex. No. | Structure | IC50 (nM) RET | Form | IC50 (nM) KDR | Form |
|---|---|---|---|---|---|
| Ex. 1 (free)/ Ex. 2 (Mesylate) | 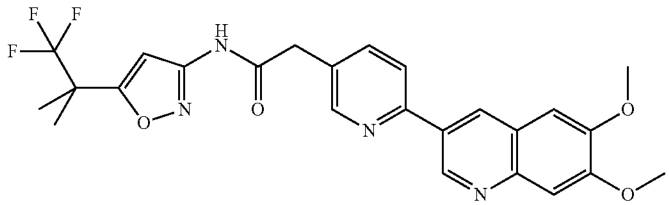 [SMILES: COc1cc2cc(-c3ccc(CC(=O)Nc4cc(C(C)(C)C(F)(F)F)on4)cn3)cnc2cc1OC] | 18 | Free | 828 | Mesylate |
| Ex. 3 (free)/ Ex. 4 (Mesylate) | 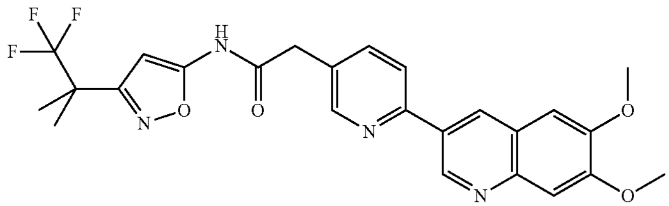 [SMILES: COc1cc2cc(-c3ccc(CC(=O)Nc4cc(C(C)(C)C(F)(F)F)no4)cn3)cnc2cc1OC] | 4 | Free | 287 | Mesylate |
| Ex. 5 (free)/ Ex. 6 (Mesylate) | 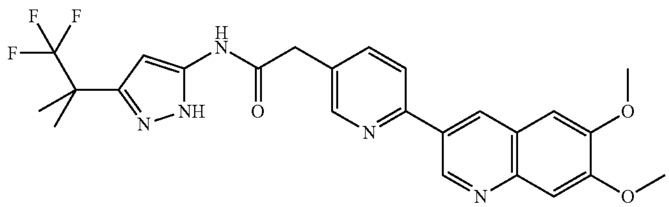 [SMILES: COc1cc2cc(-c3ccc(CC(=O)Nc4cc(C(C)(C)C(F)(F)F)n[nH]4)cn3)cnc2cc1OC] | 10 | Free | 566 | Mesylate |

TABLE 8

| WO2015/031613 Ex. No./Comp. No. | Structure | IC50 (nM) RET | Form | IC50 (nM) KDR | Form |
|---|---|---|---|---|---|
| Ex. 8 | 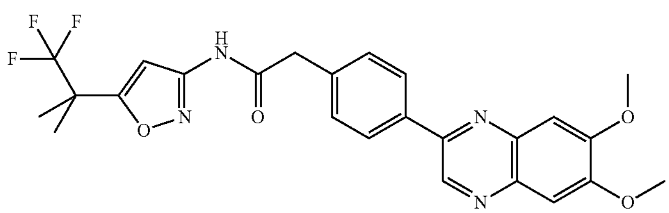 [SMILES: COc1cc2ncc(-c3ccc(CC(=O)Nc4cc(C(C)(C)C(F)(F)F)on4)cc3)nc2cc1OC] | 7 | Free | 9 | Free |
| Ex. 182 | 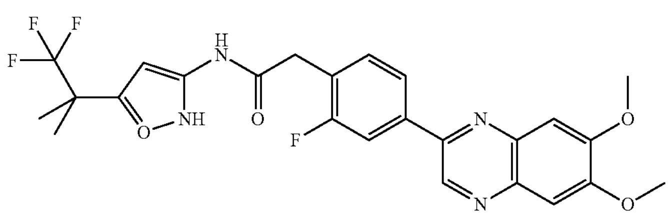 | 2 | Free | 1.5 | Free |
| Ref Ex. 1 | 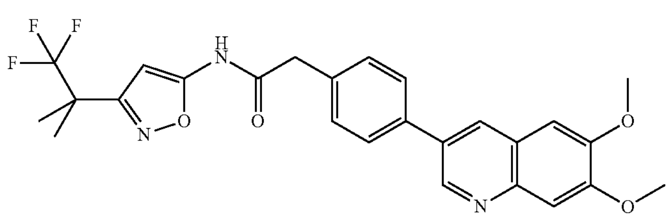 | 8 | Free | 7 | Mesylate |

TABLE 8-continued

| WO2015/031613 Ex. No./Comp. No. | Structure | IC50 (nM) RET | Form | IC50 (nM) KDR | Form |
|---|---|---|---|---|---|
| Ref Ex. 2 | (structure) | 5 | Free | 16 | Free |
| Ref Ex. 3 | (structure) | 8 | Free | 6 | Free |

[Comparative Data 2] One Shot PKPD Analysis

Murine pro-B cells, Ba/F3, expressing fusion protein of ets variant 6 (ETV)-RET and ETV-RET-V804L were constructed by Daiichi Sankyo RD Novare Co., Ltd., and cultivated in RPMI1640 medium (Thermo Fisher Scientific K.K.) supplemented with 10% (v/v) heat-inactivated fetal bovine serum (FBS, GE Healthcare) and 1.5 pg/mL puromycin in a $CO_2$ incubator that was set at 37° C. with a 5% $CO_2$ atmosphere. The cells were suspended in DPBS and inoculated subcutaneously into mice at $1.0 \times 10^7$ cells per mouse. After the tumor had reached a size of 100 to 200 $mm^3$, the mice were randomized based on tumor diameter and the test compounds (10 mg/kg, Compound 229 or Example 3) which were dissolved in 1% (w/v) hydroxypropyl methylcellulose solution were administrated orally. Control group was administrated with 1% (w/v) hydroxypropyl methylcellulose solution. Six hours after administration, tumors were harvested and frozen by liquid nitrogen immediately. The frozen samples were homogenized by bead mill homogenizer (Biomedical Science Co., Ltd., and Yasui Kikai Corporation) with lysis buffer (Cell Signaling Technology, Inc.) and protease and phosphatase inhibitor cocktail (Roche Diagnostics GmbH). Protein concentration of tumor lysate was quantified by colorimetric reagent (Thermo Fisher Scientific K.K.) and all were diluted to the same concentration by lysis buffer. Tumor lysate was added to sample buffer with a reducing reagent (Thermo Fisher Scientific K.K.) and denatured by heat (70° C., 10 minutes). 30 pg, 15 pg and 15 pg of protein were used to detect the expression of phospho-RET, RET and Actin, respectively. Protein was resolved on 5% to 20% tris HCl gels (DRC Co., Ltd.) and transferred to nitrocellulose membranes (Thermo Fisher Scientific K.K.). The membranes were blotted with anti-RET rabbit monoclonal antibody (1:1000 dilution, Cat. No. 14698, Cell Signaling Technology, Inc.), anti-phospho RET (Y905) rabbit polyclonal antibody (1:250 dilution, Cat. No. 3221, Cell Signaling Technology, Inc.), and anti-Actin rabbit polyclonal antibody (1:4000 dilution, Cat. No. sc-1616R, Santa Cruz Biotechnology, Inc.) primary antibodies followed by anti-rabbit IgG goat antibody HRP-conjugated secondary antibody (1:2000 dilution, Cat. No. 7074, Cell Signaling Technology, Inc.). The chemiluminescence reaction of HRP and the substrate (Pierce ECL Plus Western Blotting Substrate, Cat. No. 32132, Thermo Fisher Scientific K.K.) was detected by an image scanner Typhoon 9400 (GE Healthcare). Signal intensities fo phosphorylated RET (pRET) and RET were quantified and calculated as following methods.

Phosphorylation ratio of RET: (Signal intensity of pRET)/(Signal intensity of RET)

Relative phosphorylation of RET (%): [(mean phosphorylation ratio of RET in test compound treated samples)/(mean phosphorylation ratio of RET in vehicle treated samples)]×100

TABLE 9

|  | Biochemical assay (non-cell system) | | In vivo assay | |
|---|---|---|---|---|
|  | $IC_{50}$ (nM) RET-WT | $IC_{50}$ (nM) RET-V804L | Relative phosphorylation of RET (%) in Ba/F3-RET tumors (Dose: 10 mg/kg) | Relative phosphorylation of RET (%) in Ba/F3-RET-V804M tumors (Dose: 10 mg/kg) |
| Compound 229* | 1.5 | 1.7 | NT | 98 |
| Example 3 | 4.6 | 6.3 | 6 | NT |

NT: Not tested
*Compound 229 has a following structure and is described in WO2015/031613 as Example Number 229.

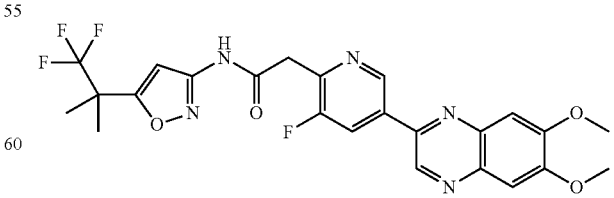

Compound 229 did not suppress phosphorylated RET (pRET) in Ba/F3-RET-V804M tumors due to poor exposure in tumors (data available), although Comp. 229 showed strong inhibitory effect in vitro. Poor exposure could be the main reason of weak potency in vivo of Compound 229. On the other hand, compound of Example 3 clearly inhibited pRET in Ba/F3-RET tumors.

Formulation Examples

<Formulation Example 1> Capsule Agent

| Compound of Example 4 or 6 | 50 mg |
|---|---|
| Lactose | 128 mg |
| Corn starch | 70 mg |
| Magnesium stearate | 2 mg |
| | 250 mg |

The powder having the above prescription was mixed, and then passed through a sieve with 60 meshes. Thereafter, this powder was placed in 250 mg of a gelatin capsule to prepare a capsule agent.

<Formulation Example 2> Tablet Agent

| Compound of Example 4 or 6 | 50 mg |
|---|---|
| Lactose | 126 mg |
| Corn starch | 23 mg |
| Magnesium stearate | 1 mg |
| | 200 mg |

The powder having the above prescription was mixed, and thereafter, the mixture was granulated using corn starch paste and then dried. Using a tablet-making machine, tablets were made from the reaction mixture (single tablet: 200 mg). These tablets can be coated with sugar, as necessary.

INDUSTRIAL APPLICABILITY

The novel pyridine compound represented by the above described general formula (I) of the present invention, or a salt thereof, or a solvate thereof has excellent RET kinase inhibiting action and is useful as a medicament.

The invention claimed is:

1. A compound represented by the following general formula (I):

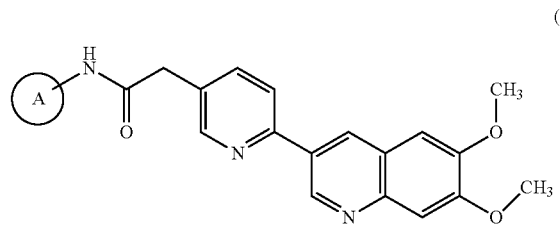

wherein A represents one selected from the following formulae (Ia) to (Id):

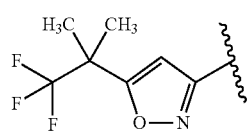

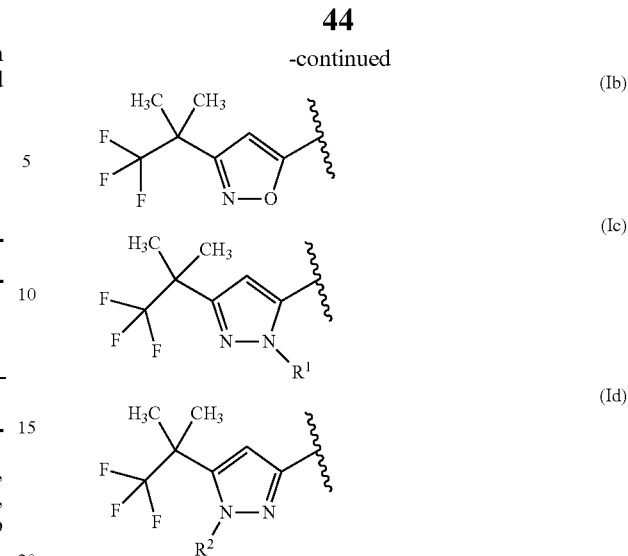

wherein $R^1$ represents a hydrogen atom or a $C_1$-$C_3$ alkyl group, and $R^2$ represents a hydrogen atom or a $C_1$-$C_3$ alkyl group, or a pharmaceutically acceptable salt thereof.

2. The compound of claim 1, of the formula:

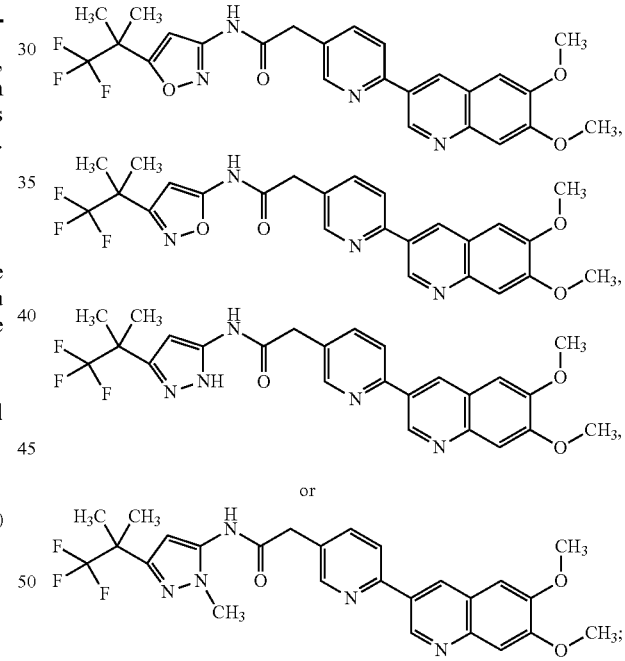

or a pharmaceutically acceptable salt thereof.

3. The compound of claim 1, which is 2-[6-(6,7-Dimethoxyquinolin-3-yl)pyridin-3-yl]-N-[5-(1,1,1-trifluoro-2-methylpropan-2-yl)-1,2-oxazol-3-yl]acetamide, or a pharmaceutically acceptable salt thereof.

4. The compound of claim 1, which is 2-[6-(6,7-Dimethoxyquinolin-3-yl)pyridin-3-yl]-N-[3-(1,1,1-trifluoro-2-methylpropan-2-yl)-1,2-oxazol-5-yl]acetamide, or a pharmaceutically acceptable salt thereof.

5. The compound of claim 1, which is 2-[6-(6,7-Dimethoxyquinolin-3-yl)pyridin-3-yl]-N-[3-(1,1,1-trifluoro-2-methylpropan-2-yl)-1H-pyrazol-5-yl]acetamide, or a pharmaceutically acceptable salt thereof.

6. The compound of claim 1, which is 2-[6-(6,7-Dimethoxyquinolin-3-yl)pyridin-3-yl]-N-[1-methyl-3-(1,1,1-trifluoro-2-methylpropan-2-yl)-1H-pyrazol-5-yl]acetamide, or a pharmaceutically acceptable salt thereof.

7. The compound according to claim 2 as a pharmaceutically acceptable salt thereof.

8. The compound of claim 7, wherein the pharmaceutically acceptable salt is a methanesulfonate salt.

9. A pharmaceutical composition comprising a compound of claim 1 or a pharmaceutically acceptable salt thereof, and one or more pharmaceutically acceptable excipients.

10. The compound of claim 3 as a pharmaceutically acceptable salt.

11. The compound of claim 4 as a pharmaceutically acceptable salt.

12. The compound of claim 5 as a pharmaceutically acceptable salt.

13. The compound of claim 6 as a pharmaceutically acceptable salt.

* * * * *